(12) United States Patent
Messerly et al.

(10) Patent No.: US 10,736,649 B2
(45) Date of Patent: Aug. 11, 2020

(54) ELECTRICAL AND THERMAL CONNECTIONS FOR ULTRASONIC TRANSDUCER

(71) Applicant: Ethicon LLC, Guaynabo, PR (US)

(72) Inventors: Jeffrey D. Messerly, Cincinnati, OH (US); Craig T. Davis, Cincinnati, OH (US); Mark E. Tebbe, Lebanon, OH (US); Brian D. Black, Loveland, OH (US); Stephen M. Leuck, Milford, OH (US); Eric M. Roberson, Lebanon, OH (US); John E. Brady, Cincinnati, OH (US); Amrita S. Sawhney, Cincinnati, OH (US); Shan Wan, Mason, OH (US); Ion V Nicolaescu, Cincinnati, OH (US); James M. Wilson, Cincinnati, OH (US); Amelia A. Pierce, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 200 days.

(21) Appl. No.: 15/679,952

(22) Filed: Aug. 17, 2017

(65) Prior Publication Data

US 2018/0055531 A1 Mar. 1, 2018

Related U.S. Application Data

(60) Provisional application No. 62/379,550, filed on Aug. 25, 2016.

(51) Int. Cl.
*A61B 17/32* (2006.01)
*H01L 41/053* (2006.01)
(Continued)

(52) U.S. Cl.
CPC .............. *A61B 17/320068* (2013.01); *A61B 17/00234* (2013.01); *A61N 7/02* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 6,669,690 | B1* | 12/2003 | Okada | A61B 17/320092 606/40 |
| 2002/0165577 | A1* | 11/2002 | Witt | A61B 17/320092 606/205 |
| 2004/0204728 | A1* | 10/2004 | Haefner | A61N 1/05 606/169 |
| 2011/0196398 | A1* | 8/2011 | Robertson | A61B 17/32002 606/169 |
| 2016/0240768 | A1* | 8/2016 | Fujii | H01L 41/0471 |

OTHER PUBLICATIONS https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
(Continued)

*Primary Examiner* — Bryan P Gordon

(57) ABSTRACT

Disclosed is an ultrasonic surgical instrument comprising a transducer base plate, first and second piezoelectric elements positioned on opposite faces of the transducer base plate. The transducer base plate is coupled to a waveguide. The waveguide is electrically coupled to the first and second piezoelectric elements by a conductive adhesive. The first and second piezoelectric elements are electrically coupled to an ultrasonic signal generator through an electrode. A thermal conductor conducts thermal energy away from the first and second piezoelectric elements. Also disclosed is a method of fabricating such an ultrasonic surgical instrument.

13 Claims, 25 Drawing Sheets

(51) Int. Cl.
*H01L 41/083* (2006.01)
*H01L 41/09* (2006.01)
*A61B 17/00* (2006.01)
*B29C 65/48* (2006.01)
*A61N 7/02* (2006.01)
*A61B 17/22* (2006.01)
*A61B 17/29* (2006.01)
*B29L 31/00* (2006.01)
*A61B 17/16* (2006.01)
*A61B 18/00* (2006.01)

(52) U.S. Cl.
CPC ...... *B29C 65/4805* (2013.01); *H01L 41/0536* (2013.01); *H01L 41/083* (2013.01); *H01L 41/0835* (2013.01); *H01L 41/0986* (2013.01); *A61B 17/1628* (2013.01); *A61B 2017/00017* (2013.01); *A61B 2017/0088* (2013.01); *A61B 2017/00402* (2013.01); *A61B 2017/00477* (2013.01); *A61B 2017/00526* (2013.01); *A61B 2017/22027* (2013.01); *A61B 2017/294* (2013.01); *A61B 2017/32007* (2017.08); *A61B 2017/320074* (2017.08); *A61B 2017/320082* (2017.08); *A61B 2017/320088* (2013.01); *A61B 2017/320089* (2017.08); *A61B 2017/320098* (2017.08); *A61B 2018/00565* (2013.01); *A61B 2018/00589* (2013.01); *A61B 2018/00595* (2013.01); *B29L 2031/7546* (2013.01)

(56) References Cited

OTHER PUBLICATIONS

Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe,Integrated Circuit Engineering, Addison-Wesley Publishing, Reading, MA (1979). (book—not attached).
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.

* cited by examiner

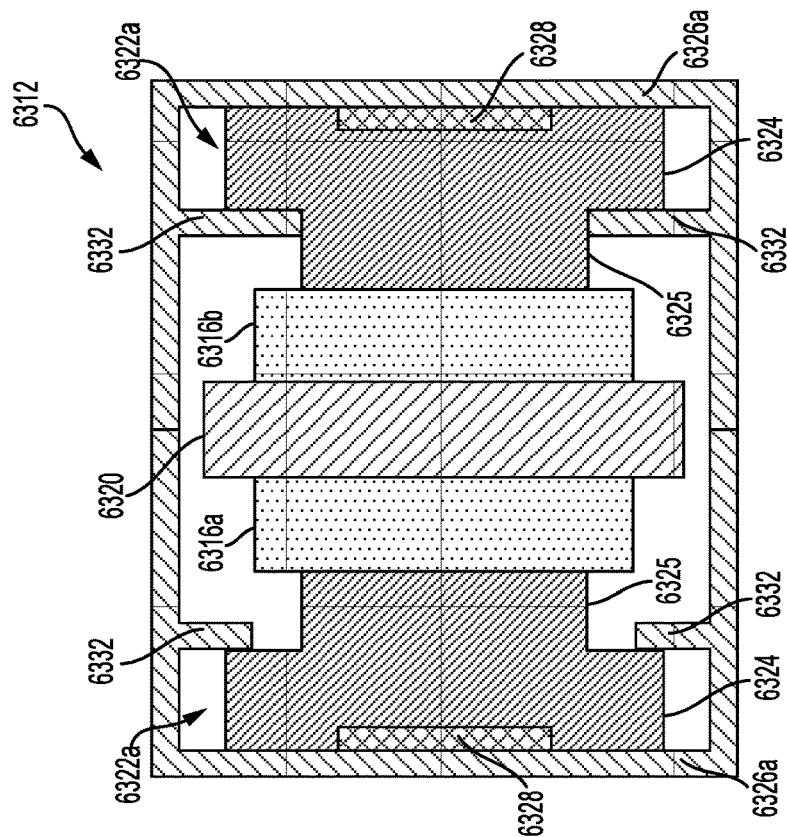
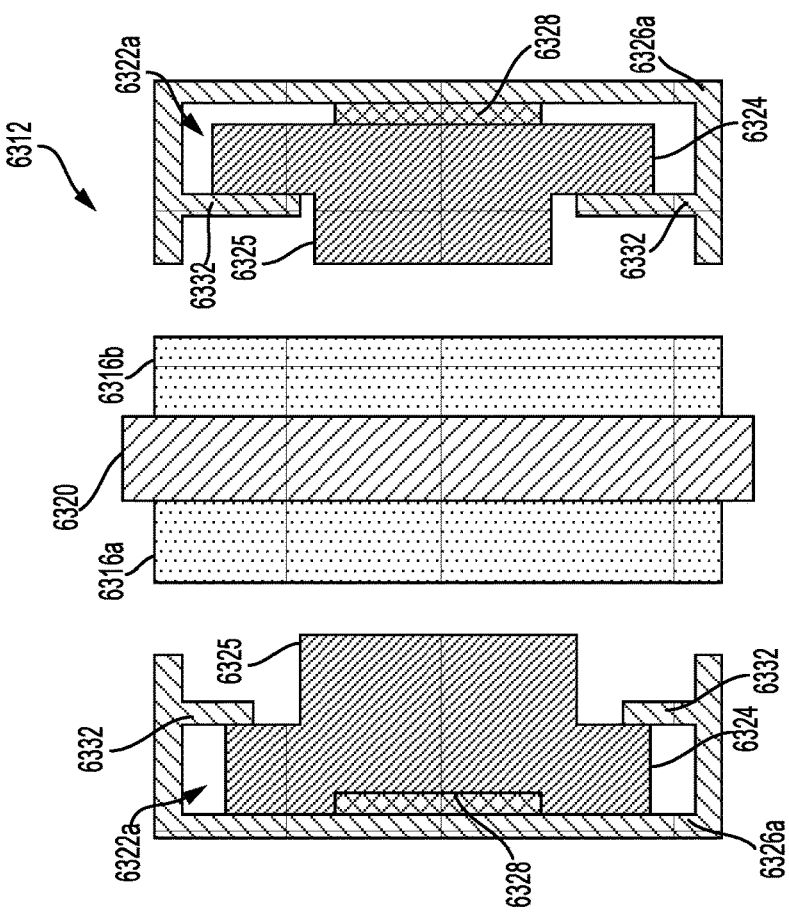
FIG. 23A
FIG. 23B

ELECTRICAL AND THERMAL CONNECTIONS FOR ULTRASONIC TRANSDUCER

PRIORITY

This application claims the benefit of U.S. Provisional Application Ser. No. 62/379,550 filed Aug. 25, 2016, which is incorporated herein by reference in its entirety.

BACKGROUND

The present disclosure relates, in general, to ultrasonic surgical instruments and more particularly to ultrasonic transducers to drive ultrasonic waveguides. Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer, through a waveguide, and to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue. Because of the nature of ultrasonic instruments, a particular ultrasonically actuated end effector may be designed to perform numerous functions, including, for example, cutting and coagulation. Ultrasonic vibration is induced in the surgical end effector by electrically exciting a transducer, for example. The transducer may be constructed of one or more piezoelectric or magnetostrictive elements in the instrument hand piece. Vibrations generated by the transducer are transmitted to the surgical end effector via an ultrasonic waveguide extending from the transducer to the surgical end effector. The waveguide and end effector are designed to resonate at the same frequency as the transducer. Therefore, when an end effector is attached to a transducer, the overall system frequency is the same frequency as the transducer itself.

The amplitude of the longitudinal ultrasonic vibration at the tip, d, of the end effector behaves as a simple sinusoid at the resonant frequency as given by:

$$d = A \sin(\omega t)$$

where:
ω=the radian frequency which equals 2π times the cyclic frequency, f; and
A=the zero-to-peak amplitude.

The longitudinal excursion of the end effector tip is defined as the peak-to-peak (p-t-p) amplitude, which is just twice the amplitude of the sine wave or 2A. Often, the end effector can comprise a blade which, owing to the longitudinal excursion, can cut and/or coagulate tissue. U.S. Pat. No. 6,283,981, which issued on Sep. 4, 2001 and is entitled METHOD OF BALANCING ASYMMETRIC ULTRASONIC SURGICAL BLADES; U.S. Pat. No. 6,309,400, which issued on Oct. 30, 2001 and is entitled CURVED ULTRASONIC WAVEGUIDE HAVING A TRAPEZOIDAL CROSS SECTION; and U.S. Pat. No. 6,436,115, which issued on Aug. 20, 2002 and is entitled BALANCED ULTRASONIC WAVEGUIDE INCLUDING A PLURALITY OF BALANCE ASYMMETRIES, the entire disclosures of which are hereby incorporated by reference herein, disclose various ultrasonic surgical instruments.

SUMMARY

In one general aspect, various aspects are directed to an ultrasonic surgical instrument that comprises a transducer configured to produce vibrations along a longitudinal axis of a surgical tool at a predetermined frequency. In various aspects, the surgical tool may include an ultrasonic waveguide that extends along the longitudinal axis and is coupled to the transducer. In various aspects, the surgical tool includes a body having a proximal end and a distal end, wherein the distal end is movable relative to the longitudinal axis by the vibrations produced by the transducer, and the proximal end is mechanically coupled to the transducer.

In one aspect, an ultrasonic surgical instrument is provided. The ultrasonic surgical instrument comprises a transducer base plate (e.g., a transducer mounting portion) comprising a first and second face; a first piezoelectric element positioned on the first face; a second piezoelectric element positioned on the second face, wherein the first and second piezoelectric element are each configured to operate in a D31 mode with respect to a longitudinal axis of a waveguide coupled to the transducer base plate, wherein the waveguide is electrically coupled to the first piezoelectric element and to the second piezoelectric element by a conductive adhesive; an electrode configured to electrically couple the first and second piezoelectric elements to an ultrasonic signal generator; and a thermal conductor configured to conduct thermal energy away from the first and second piezoelectric elements.

In another aspect, a method of fabricating an ultrasonic surgical instrument is provided. The method comprises machining a transducer base plate from a portion of a flat metal stock, wherein the transducer base plate comprises a first and second face; positioning a first piezoelectric element on the first face; positioning a second piezoelectric element on the second face, wherein the first and second piezoelectric element are each configured to operate in a D31 mode with respect to a longitudinal axis of a waveguide coupled to the transducer base plate; coupling, by a first electrically conductive adhesive, the waveguide to the first piezoelectric element and the second piezoelectric element; compressing, by an electrode, against the first and second piezoelectric elements to electrically couple the first and second piezoelectric elements to an ultrasonic signal generator; and conducting, by a thermal conductor, heat away from the first and second piezoelectric elements.

In another aspect, a transducer base plate is provided. The transducer base plate comprises a first and second face, wherein a first piezoelectric element is positioned on the first face and a second piezoelectric element is positioned on the second face, and wherein the first and second piezoelectric element are each configured to operate in a D31 mode with respect to a longitudinal axis of a waveguide coupled to the transducer base plate; a conductive adhesive to electrically couple the first and second piezoelectric elements to the waveguide; an electrode configured to electrically couple the first and second piezoelectric elements to an ultrasonic signal generator; and a thermal conductor configured to conduct heat away from the first and second piezoelectric elements.

In another aspect, an ultrasonic transducer assembly is provided. The ultrasonic transducer assembly comprises a stack of a plurality of piezoelectric elements, wherein the stack is configured to operate in a D33 mode with respect to a longitudinal axis of a waveguide coupled to the transducer base plate; a compression plate to compress the stack of the plurality of piezoelectric elements to couple the stack of piezoelectric elements to a waveguide; and a compressive element for applying a compressive force against the compression plate.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIGS. 23A-23B illustrate an assembly process of the transducer assembly shown in FIG. 20, with electrodes assembled from an initial uncompressed state to a final compressed state, according to one aspect of this disclosure.

DESCRIPTION

Figure 1:
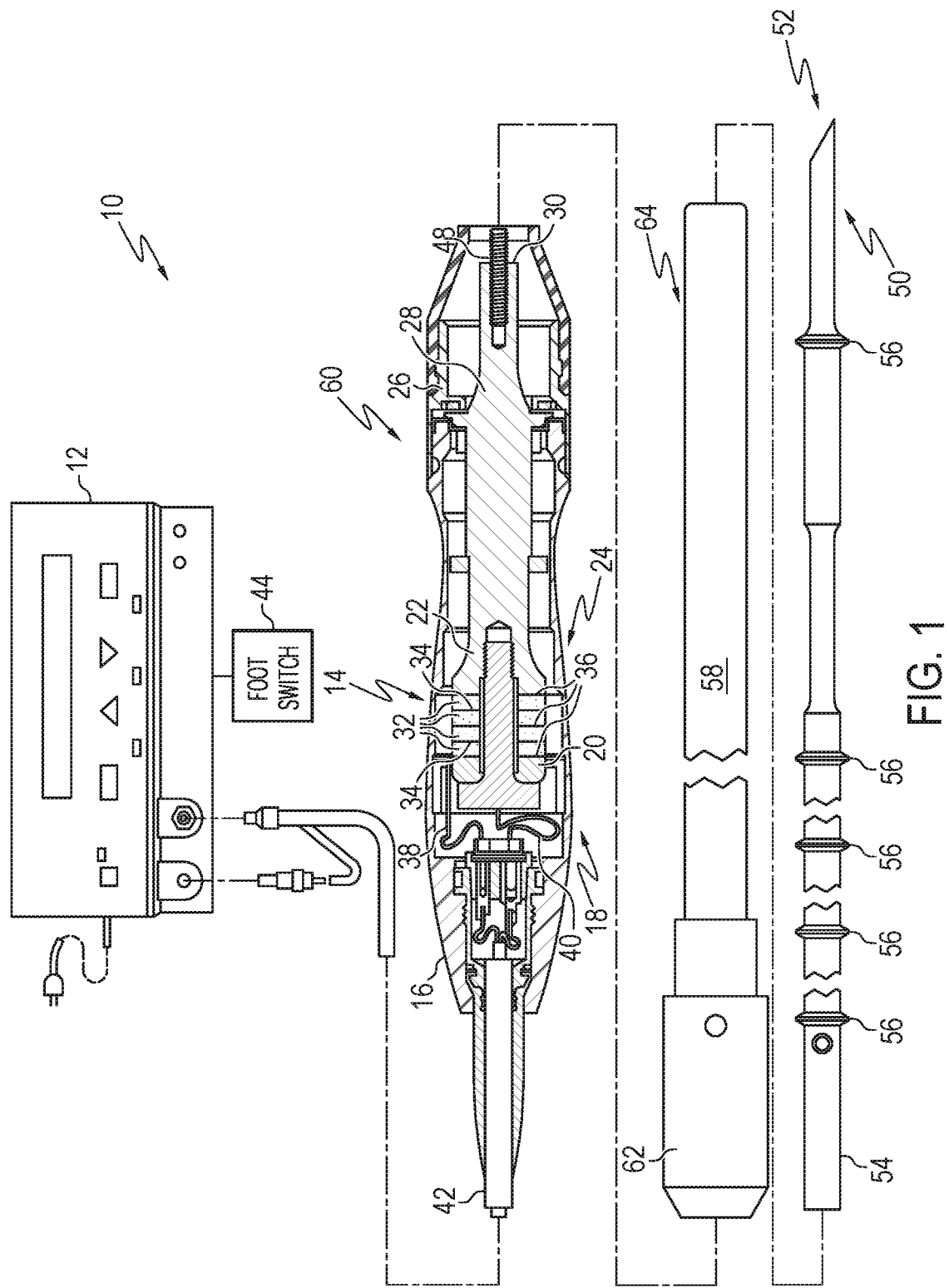
FIG. 1 illustrates an ultrasonic surgical instrument system, according to one aspect of this disclosure.

Applicant of the present application owns the following patent applications filed Aug. 17, 2017 and which are each herein incorporated by reference in their respective entireties:

U.S. patent application Ser. No. 15/679,940, titled "Ultrasonic Transducer Techniques for Ultrasonic Surgical Instrument" by inventors jeffrey Messerly et al. filed Aug. 17, 2017.

U.S. patent application Ser. No. 15/679,948, titled "Ultrasonic Transducer For Surgical Instrument, by inventors Jeffrey Messerly et al. filed Aug. 17, 2017.

U.S. patent application Ser. No. 15/679,959, titled "Ultrasonic Transducer To Waveguide Acoustic Coupling, Connections, and Configurations" by inventors Jeffrey Messerly et al. filed Aug. 17, 2017.

U.S. patent application Ser. No. 15/679,960, titled "Ultrasonic Transducer to Waveguide Joining" by inventors Jeffrey Messerly et al. filed Aug. 17, 2017.

U.S. patent application Ser. No. 15/679,967, titled "Tissue Loading of a Surgical Instrument" by inventors Jeffrey Messerly et al. filed Aug. 17, 2017.

Before explaining various aspects in detail, it should be noted that such aspects are not limited in their application or use to the details of construction and arrangement of parts illustrated in the accompanying drawings and description. The illustrative aspects may be implemented or incorporated in other aspects, variations and modifications, and may be practiced or carried out in various ways. For example, the surgical instruments disclosed below are illustrative only and not meant to limit the scope or application thereof. Furthermore, unless otherwise indicated, the terms and expressions employed herein have been chosen for the purpose of describing the illustrative aspects for the convenience of the reader and are not to limit the scope thereof.

Certain aspects will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples aspects and that the scope of the various aspects is defined solely by the claims. The features illustrated or described in connection with one aspect may be combined with the features of other aspects. Such modifications and variations are intended to be included within the scope of the claims.

Various aspects described herein relate, in general, to ultrasonic surgical instruments and blades for use therewith. Examples of ultrasonic surgical instruments and blades are disclosed in U.S. Pat. Nos. 5,322,055; 5,954,736; 6,309,400; 6,278,218; 6,283,981; 6,325,811; and 8,319,400, wherein the entire disclosures of which are incorporated by reference herein.

According to various aspects of the present disclosure, various methods of electrically coupling components of a surgical tool are disclosed. The surgical tool may be a component of an ultrasonic surgical instrument.

FIG. 1 illustrates one aspect of an ultrasonic system 10. One aspect of the ultrasonic system 10 comprises an ultrasonic signal generator 12 coupled to an ultrasonic transducer 14, a hand piece assembly 60 comprising a hand piece housing 16, and an end effector 50. The ultrasonic transducer 14, which is known as a "Langevin stack," generally includes a transduction portion 18, a first resonator or end-bell 20, and a second resonator or fore-bell 22, and ancillary components. In various aspects, the ultrasonic transducer 14 is preferably an integral number of one-half system wavelengths ($n\lambda/2$) in length as will be described in more detail below. An acoustic assembly 24 can include the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude of the velocity transformer 28, or, alternately, fore-bell 22 may have no amplification.

Referring again to FIG. 1, end-bell 20 can include a threaded member extending therefrom which can be configured to be threadably engaged with a threaded aperture in fore-bell 22. In various aspects, piezoelectric elements, such as piezoelectric elements 32, for example, can be compressed between end-bell 20 and fore-bell 22 when end-bell 20 and fore-bell 22 are assembled together. Piezoelectric elements 32 may be fabricated from any suitable material, such as, for example, lead zirconate-titanate, lead meta-niobate, lead titanate, and/or any suitable piezoelectric crystal material, for example.

In various aspects, as discussed in greater detail below, transducer 14 can further comprise electrodes, such as positive electrodes 34 and negative electrodes 36, for example, which can be configured to create a voltage potential across one or more piezoelectric elements 32. Each of the positive electrodes 34, negative electrodes 36, and the piezoelectric elements 32 can comprise a bore extending through the center which can be configured to receive the threaded member of end-bell 20. In various aspects, the positive and negative electrodes 34 and 36 are electrically coupled to wires 38 and 40, respectively, wherein the wires 38 and 40 can be encased within a cable 42 and electrically connectable to the ultrasonic signal generator 12 of the ultrasonic system 10.

In various aspects, the ultrasonic transducer 14 of the acoustic assembly 24 converts the electrical signal from the ultrasonic signal generator 12 into mechanical energy that results in primarily longitudinal vibratory motion of the ultrasonic transducer 24 and the end effector 50 at ultrasonic frequencies. A suitable generator is available as model number GEN11, from Ethicon Endo-Surgery, Inc., Cincinnati, Ohio. When the acoustic assembly 24 is energized, a vibratory motion standing wave is generated through the acoustic assembly 24. A suitable vibrational frequency range may be about 20 Hz to 120 kHz and a well-suited vibrational frequency range may be about 30-70 kHz and one example operational vibrational frequency may be approximately 55.5 kHz.

The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda/4$).

As outlined above, the wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44, for example, to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy.

In various aspects, the ultrasonic energy produced by transducer 14 can be transmitted through the acoustic assembly 24 to the end effector 50 via an ultrasonic transmission waveguide 46. In order for the acoustic assembly 24 to deliver energy to the end effector 50, the components of the acoustic assembly 24 are acoustically coupled to the end effector 50. For example, the distal end of the ultrasonic transducer 14 may be acoustically coupled at the surface 30 to the proximal end of the ultrasonic transmission waveguide 46 by a threaded connection such as a stud 48.

The components of the acoustic assembly 24 can be acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths ($\lambda/2$). A distal end 52 of the ultrasonic end effector 50 may be disposed at, or at least near, an antinode in order to provide the maximum, or at least nearly maximum, longitudinal excursion of the distal end. When the transducer assembly is energized, in various aspects, the distal end 52 of the ultrasonic end effector 50 may be configured to move in the range of, for example, approximately 10 to 500 microns peak-to-peak and preferably in the range of approximately 30 to 150 microns at a predetermined vibrational frequency.

As outlined above, the ultrasonic end effector 50 may be coupled to the ultrasonic transmission waveguide 46. In various aspects, the ultrasonic end effector 50 and the ultrasonic transmission guide 46 as illustrated are formed as a single unit construction from a material suitable for transmission of ultrasonic energy such as, for example, Ti6Al4V (an alloy of titanium including aluminum and vanadium), aluminum, stainless steel, and/or any other suitable material. Alternately, the ultrasonic end effector 50 may be separable (and of differing composition) from the ultrasonic transmission waveguide 46, and coupled by, for example, a stud, weld, glue, quick connect, or other suitable known methods. The ultrasonic transmission waveguide 46 may have a length substantially equal to an integral number of one-half system wavelengths ($\lambda/2$), for example. The ultrasonic transmission waveguide 46 may be preferably fabricated from a solid core shaft constructed out of material that propagates ultrasonic energy efficiently, such as titanium alloy (i.e., Ti6Al4V) or an aluminum alloy, for example.

In the aspect illustrated in FIG. 1, the ultrasonic transmission waveguide 46 comprises a plurality of stabilizing silicone rings or compliant supports 56 positioned at, or at least near, a plurality of nodes. The silicone rings 56 can dampen undesirable vibration and isolate the ultrasonic energy from a sheath 58 at least partially surrounding waveguide 46, thereby assuring the flow of ultrasonic energy in a longitudinal direction to the distal end 52 of the end effector 50 with maximum efficiency.

As shown in FIG. 1, the sheath 58 can be coupled to the distal end of the handpiece assembly 60. The sheath 58 generally includes an adapter or nose cone 62 and an elongated tubular member 64. The tubular member 64 is attached to and/or extends from the adapter 62 and has an opening extending longitudinally therethrough. In various aspects, the sheath 58 may be threaded or snapped onto the distal end of the housing 16. In at least one aspect, the ultrasonic transmission waveguide 46 extends through the opening of the tubular member 64 and the silicone rings 56 can contact the sidewalls of the opening and isolate the ultrasonic transmission waveguide 46 therein. In various aspects, the adapter 62 of the sheath 58 is preferably constructed from Ultem®, for example, and the tubular member 64 is fabricated from stainless steel, for example. In at least one aspect, the ultrasonic transmission waveguide 46 may have polymeric material, for example, surrounding it in order to isolate it from outside contact.

As described above, a voltage, or power source can be operably coupled with one or more of the piezoelectric elements of a transducer, wherein a voltage potential applied to each of the piezoelectric elements can cause the piezoelectric elements to expand and contract, or vibrate, in a longitudinal direction. As also described above, the voltage potential can be cyclical and, in various aspects, the voltage potential can be cycled at a frequency which is the same as, or nearly the same as, the resonant frequency of the system of components comprising transducer 14, wave guide 46, and end effector 50, for example. In various aspects, however, certain of the piezoelectric elements within the transducer may contribute more to the standing wave of longitudinal vibrations than other piezoelectric elements within the transducer. More particularly, a longitudinal strain profile may develop within a transducer wherein the strain profile may control, or limit, the longitudinal displacements that some of the piezoelectric elements can contribute to the standing wave of vibrations, especially when the system is being vibrated at or near its resonant frequency.

It may be recognized, in reference to the ultrasonic surgical instrument system 10 of FIG. 1, that multiple components may be required to couple the mechanical vibrations from the piezoelectric elements 32 through the wave guide 46 to the end effector 50. The additional elements comprising the acoustic assembly 24 may add additional manufacturing costs, fabrication steps, and complexity to the system. Disclosed below are aspects of an ultrasonic medical device that may require fewer components, manufacturing steps, and costs than the equivalent device illustrated in FIG. 1 and as disclosed above.

Again, referring to FIG. 1, the piezoelectric elements 32 are configured into a "Langevin" stack, in which the piezoelectric elements 32 and their activating electrodes 34 and 36 (together, transducer 14) are interleaved. The mechanical vibrations of the activated piezoelectric elements 32 propagate along the longitudinal axis of the transducer 14, and are coupled via the acoustic assembly 24 to the end of the waveguide 46. Such a mode of operation of a piezoelectric element is frequently described as the D33 mode of the element, especially for ceramic piezoelectric elements comprising, for example, lead zirconate-titanate, lead metaniobate, or lead titanate. The D33 mode of a ceramic piezoelectric element is illustrated in FIGS. 2A-2C.

Figure 2A:
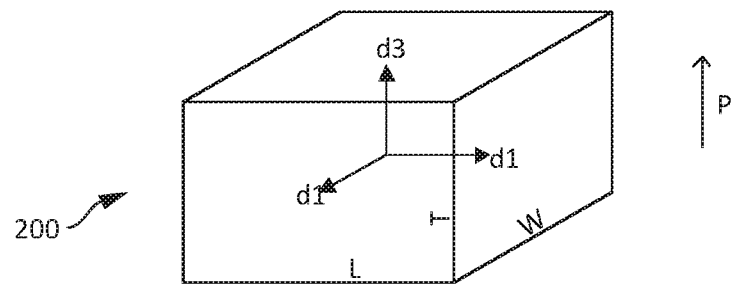
FIGS. 2A-2C illustrate a piezoelectric transducer, according to one aspect of this disclosure.

FIG. 2A depicts a piezoelectric element 200 fabricated from a ceramic piezoelectric material. A piezoelectric ceramic material is a polycrystalline material comprising a plurality of individual microcrystalline domains. Each microcrystalline domain possesses a polarization axis along which the domain may expand or contract in response to an imposed electric field. However, in a native ceramic, the polarization axes of the microcrystalline domains are arranged randomly, so there is no net piezoelectric effect in the bulk ceramic. A net re-orientation of the polarization axes may be induced by subjecting the ceramic to a temperature above the Curie temperature of the material and placing the material in a strong electrical field. Once the temperature of the sample is dropped below the Curie temperature, a majority of the individual polarization axes will be re-oriented and fixed in a bulk polarization direction. FIG. 2A illustrates such a piezoelectric element 200 after being polarized along the inducing electric field axis P. While the un-polarized piezoelectric element 200 lacks any net piezoelectric axis, the polarized element 200 can be described as possessing a polarization axis, d3, parallel to the inducing field axis P direction. For completeness, an axis orthogonal to the d3 axis may be termed a d1 axis. The dimensions of the piezoelectric element 200 are labeled as length (L), width (W), and thickness (T).

Figure 2B:
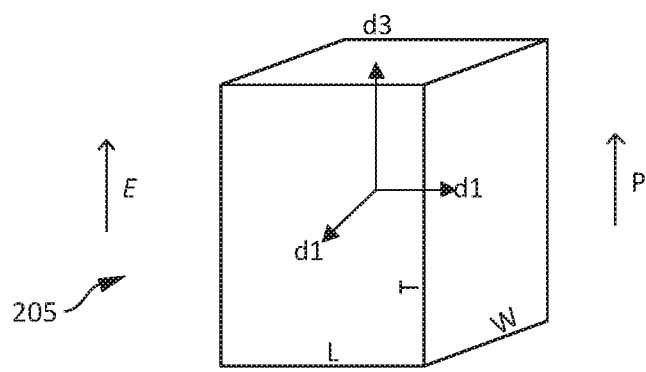
Figure 2C:
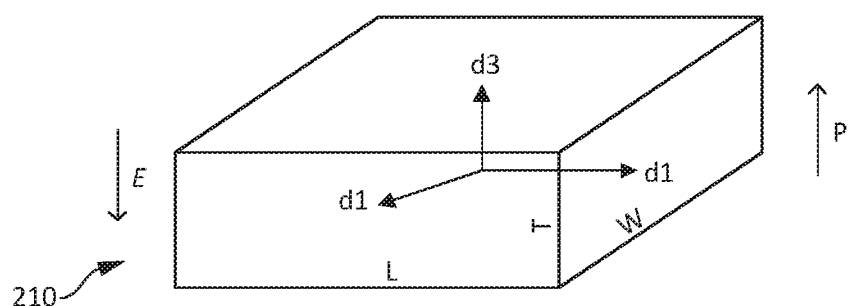

FIGS. 2B and 2C illustrate the mechanical deformations of a piezoelectric element 200 that may be induced by subjecting the piezoelectric element 200 to an actuating electrical field E oriented along the d3 (or P) axis. FIG. 2B illustrates the effect of an electric field E having the same direction as the polarization field P along the d3 axis on a piezoelectric element 205. As illustrated in FIG. 2B, the piezoelectric element 205 may deform by expanding along the d3 axis while compressing along the d1 axis. FIG. 2C illustrates the effect of an electric field E having the opposing direction to the polarization field P along the d3 axis on a piezoelectric element 210. As illustrated in FIG. 2C, the piezoelectric element 210 may deform by compressing along the d3 axis, while expanding along the d1 axis. Vibrational coupling along the d3 axis during the application of an electric field along the d3 axis may be termed D33 coupling or activation using a D33 mode of a piezoelectric element. The transducer 14 illustrated in FIG. 1 uses the D33 mode of the piezoelectric elements 32 for transmitting mechanical vibrations along the wave guide 46 to the end effector 50. Because the piezoelectric element also deforms along the d1 axis, vibrational coupling along the d1 axis during the application of an electric field along the d3 axis may also be an effective source of mechanical vibrations. Such coupling may be termed D31 coupling or activation using a D31 mode of a piezoelectric element.

As illustrated by FIGS. 2A-2C, during operation in the D31 mode, transverse expansion of piezoelectric elements 200, 205, 210 may be mathematically modeled by the following equation:

$$\frac{\Delta L}{L} = \frac{\Delta W}{W} = \frac{V_{d31}}{T}$$

In the equation, L, W, and T refer to the length, width and thickness dimensions of a piezoelectric element, respectively. $V_{d31}$ denotes the voltage applied to a piezoelectric element operating in the D31 mode. The quantity of transverse expansion resulting from the D31 coupling described above is represented by $\Delta L$ (i.e., expansion of the piezoelectric element along the length dimension) and $\Delta W$ (i.e., expansion of the piezoelectric element along the width dimension). Additionally, the transverse expansion equation models the relationship between $\Delta L$ and $\Delta W$ and the applied voltage $V_{d31}$. Disclosed below are aspects of ultrasonic medical devices based on D31 activation by a piezoelectric element.

In various aspects, as described below, a ultrasonic medical device can comprise a transducer configured to produce longitudinal vibrations, and a surgical tool having a transducer base plate operably coupled to the transducer, an end effector, and wave guide therebetween. In certain aspects, as also described below, the transducer can produce vibrations which can be transmitted to the end effector, wherein the vibrations can drive the transducer base plate, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. The transducer base plate comprises flat faces on opposite sides to receive piezoelectric elements. In various aspects, such a longitudinal strain pattern, or longitudinal stress pattern, can cause the longitudinal strain, or longitudinal stress, to vary along the length of the transducer base plate, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

Figure 3:
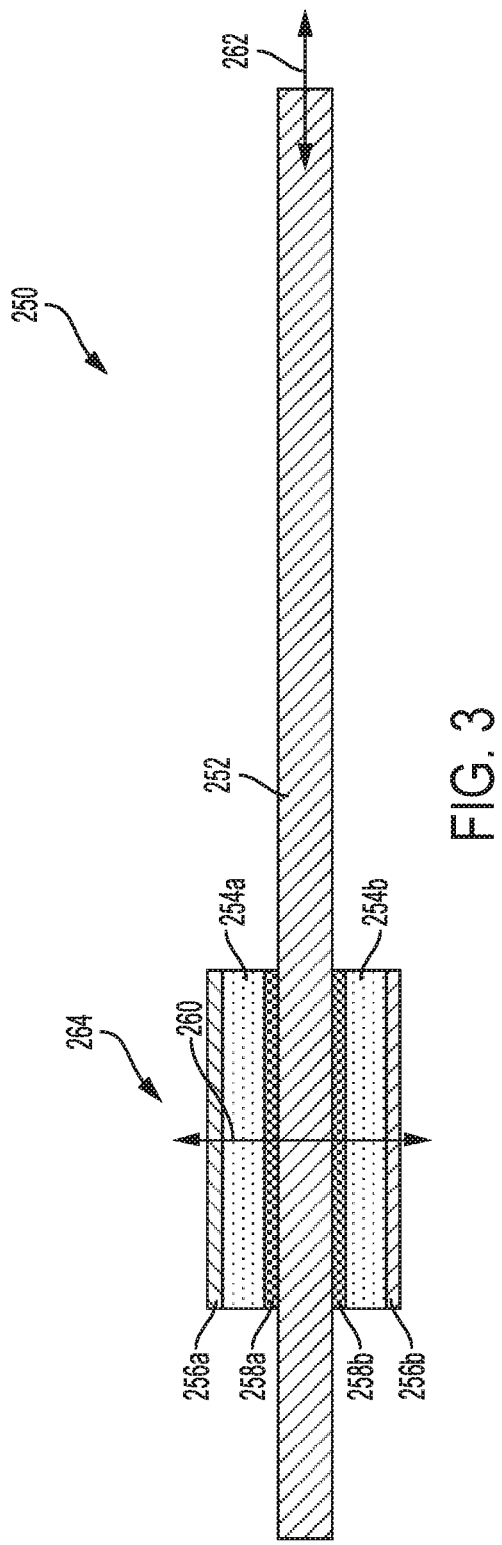
FIG. 3 illustrates a D31 ultrasonic transducer architecture that includes an ultrasonic waveguide and one or more piezoelectric elements fixed to the ultrasonic waveguide, according to one aspect of this disclosure.

FIG. 3 illustrates an ultrasonic surgical instrument 250 that includes an ultrasonic waveguide 252 attached to an ultrasonic transducer 264 by a bonding material, where the ultrasonic surgical instrument 250 is configured to operate in a D31 mode, according to one aspect of this disclosure. The ultrasonic transducer 264 includes first and second piezoelectric elements 254a, 254b attached to the ultrasonic waveguide 252 by a bonding material. The piezoelectric elements 254a, 254b include electrically conductive plates 256a, 256b to electrically couple one pole of a voltage source suitable to drive the piezoelectric elements 254a, 254b (e.g., usually a high voltage). The opposite pole of the voltage source is electrically coupled to the ultrasonic waveguide 252 by electrically conductive joints 258a, 258b. In one aspect, the electrically conductive plates 256a, 256b are coupled to a positive pole of the voltage source and the electrically conductive joints 258a, 258b are electrically coupled to ground potential through the metal ultrasonic waveguide 252. In one aspect, the ultrasonic waveguide 252 is made of titanium or titanium alloy (i.e., Ti6Al4V) and the piezoelectric elements 254a, 254b are made of a lead zirconate titanate intermetallic inorganic compound with the chemical formula $Pb[Zr_xTi_{1-x}]O_3$ ($0 \leq x \leq 1$). Also called PZT, it is a ceramic perovskite material that shows a marked piezoelectric effect, meaning that the compound changes shape when an electric field is applied. It is used in a number of practical applications such as ultrasonic transducers and piezoelectric resonators PZT. The poling axis (P) of the piezoelectric elements 254a, 254b is indicated by the direction arrow 260. The motion axis of the ultrasonic waveguide 252 in response to excitation of the piezoelectric elements 254a, 245b is shown by a motion arrow 262 at the distal end of the ultrasonic waveguide 252 generally referred to as the ultrasonic blade portion of the ultrasonic waveguide 252. The motion axis 262 is orthogonal to the poling axis (P) 260.

In conventional D33 ultrasonic transducer architectures as shown in FIG. 1, the bolted piezoelectric elements 32 utilize electrodes 34, 36 to create electrical contact to both sizes of each piezoelectric element 34. The D31 architecture 250 according to one aspect of this disclosure, however, employs a different technique to create electrical contact to both sides of each piezoelectric element 254a, 254b. Various techniques for providing electrical contact to the piezoelectric elements 254a, 254b include bonding electrical conductive elements (e.g., wires) to the free surface of each piezoelectric element 254a, 254b for the high potential connection and bonding each piezoelectric element 254a, 254b the to the ultrasonic waveguide 252 for the ground connection using solder, conductive epoxy, or other techniques described herein. Compression can be used to maintain electrical contact to the acoustic train without making a permanent connection. This can cause an increase in device thickness and should be controlled to avoid damaging the piezoelectric elements 254a, 254b. Low compression can damage the piezoelectric element 254a, 254b by a spark gap and high compression can damage the piezoelectric elements 254a, 254b by local mechanical wear. In other techniques, metallic spring contacts may be employed to create electrical contact with the piezoelectric elements 254a, 254b. Other techniques may include foil-over-foam gaskets, conductive foam, solder. Electrical connection to both sides of the piezoelectric elements 254a, 254b the D31 acoustic train configuration. The electrical ground connection can be made to the metal ultrasonic waveguide 252, which is electrically conductive, if there is electrical contact between the piezoelectric elements 254a, 254b and the ultrasonic waveguide 252.

In various aspects, as described below, an ultrasonic medical device may comprise a transducer configured to produce longitudinal vibrations, and a surgical instrument having a transducer base plate operably coupled to the transducer, an end effector, and wave guide therebetween. In certain aspects, as also described below, the transducer can produce vibrations which can be transmitted to the end effector, wherein the vibrations can drive the transducer base plate, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer base plate, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points. In conventional D33 ultrasonic transducer architectures as shown in FIG. 1, a bolt provides compression that acoustically couples the piezoelectric elements rings to the ultrasonic waveguide.

Figure 4:
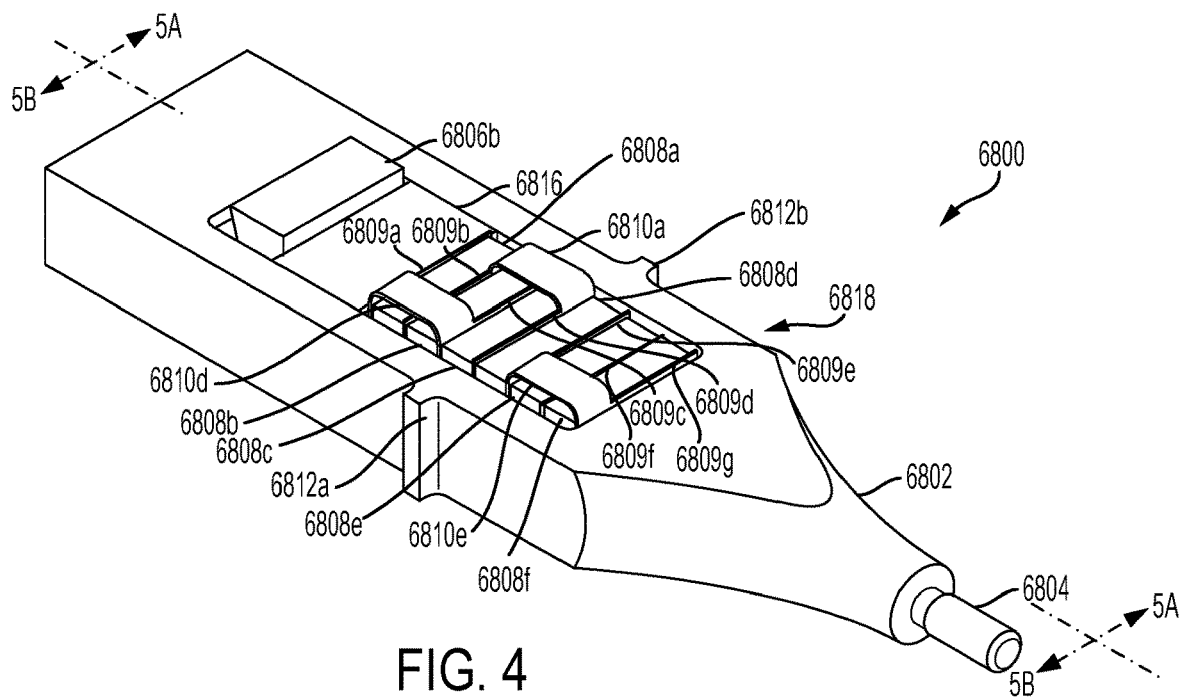
FIG. 4 is a perspective view of a transducer assembly employing a wedge configuration and configured to operate in a D33 mode of operation, according to one aspect of this disclosure.

FIG. 4 is a perspective view of a transducer assembly 6800 configured to operate in a D33 mode of operation, according to one aspect of this disclosure. The transducer assembly 6800 comprises transducer 6818, piezoelectric elements 6808a-6808f, a horn shaped portion 6802, and a threaded connection such as a stud 6804 to connect to an ultrasonic waveguide. The transducer 6818 includes piezoelectric elements 6808a-6808f. As described above, the transducer 6800 is configurable as a "Langevin" stack (e.g., with a rectangular cross section), in which the piezoelectric elements 6808a-6808f and corresponding activating electrodes 6810a-c are interleaved. In one aspect, the activating electrodes 6809a-6809g can be thin sheets of an electrically conductive metal such as, for example, aluminum, silver, gold, copper, and/or alloys thereof. The activating electrodes 6809a-g are each electrically connected to an ultrasonic signal generator via the electrically conductive elements 6810a-6810f. The electrically conductive elements 6810a, 6810b, 6810c may form a path to a pole (e.g., the positive pole) of the generator. The electrically conductive elements 6810d, 6810e, 6810f, 6810g may form another path to an opposing pole (e.g., the negative pole) of the generator. The electrically conductive elements 6810a-6810g may be U-shaped shorting caps that appear similar to brackets. As shown in FIG. 4, shorting caps 6810a-6810c are positioned over the piezoelectric elements 6808a-f. In various aspects, rather than employing a bolt to compress and acoustically couple the piezoelectric elements 6808a-6808f to an ultrasonic waveguide, the transducer assembly 6800 instead employs wedges 6806a-6806b to compress against a compressing plate 6816. In turn, the compressing plate 6816 compresses and acoustically couples the piezoelectric elements 6808 to an ultrasonic waveguide. Such compression of the piezoelectric elements 6808a-6808f can be useful for operation of the transducer 6800 stack. The compressing plate 6816 may be made of an electrically conductive metal such as steel, for example. The wedges 6806a, 6806b also may be made of an electrically conductive metal such as steel, for example.

In one aspect, the wedges 6806a (not shown in FIG. 4), 6806b can be machined and inserted by a suitable forming press. Additionally, the wedges 6806a, 6806b may be secured by a conductive bonding material or adhesive. In addition to the piezoelectric elements 6808, wedges 6806a, 6806b, electrodes 6809a-6809g, and shorting caps 6810a-6810g, the transducer assembly 6800 includes flanges 6812a, 6812b located on opposing sides of the transducer assembly 6800, such as a node location of the transducer assembly 6800. The flanges 6812a, 6812b may be configured to be received within a retainer of a housing (not shown) of an ultrasonic surgical instrument for secure attachment of the transducer assembly 6800 to the housing. Replacing the bolt with the wedges 6806a, 6806b can be advantageous because of easier machining and assembling of the transducer 6800 stack. Additional advantages of the wedge configuration include the ability to tune the acoustic assembly of the transducer assembly 6800 by modulating the tension in the transducer 6800 with the wedges 6806a, 6806b and the relatively inexpensive, simple geometric shape of the piezoelectric elements 6808a-6808f.

Figure 5A:
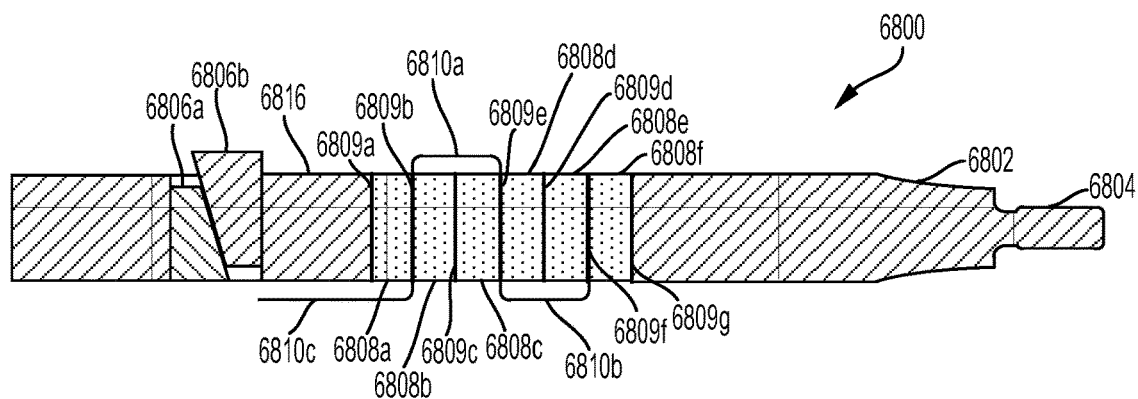
FIG. 5A is a section view of the ultrasonic transducer assembly shown in FIG. 4 taken along section line 5A-5A shown in FIG. 4, according to one aspect of this disclosure.
Figure 5B:
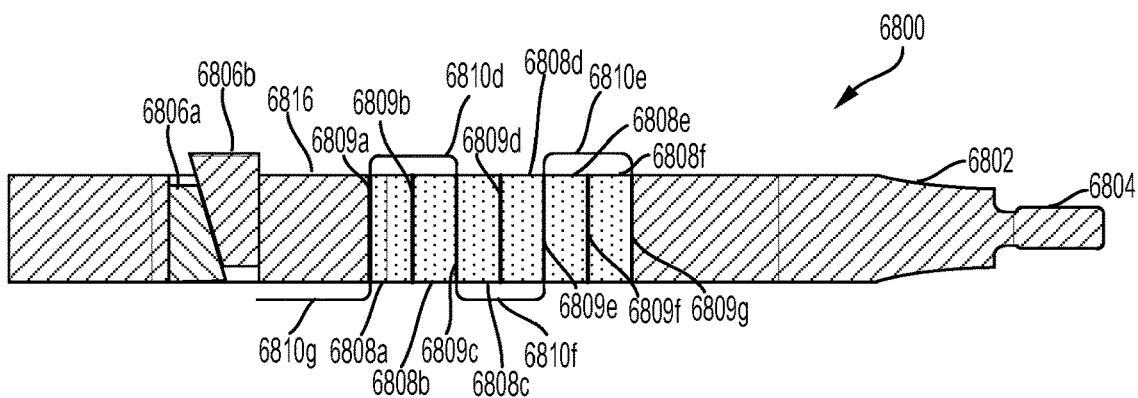
FIG. 5B is a section view of the ultrasonic transducer assembly shown in FIG. 4 taken along section line 5B-5B shown in FIG. 4, according to one aspect of this disclosure.

FIGS. 5A-5B illustrate cross section views of the ultrasonic transducer assembly 6800 employing the wedge configuration, according to one aspect of this disclosure, where FIG. 5A is a section view taken along section line 5A-5A as shown in FIG. 4 and FIG. 5B is a section view taken along section line 5B-5B as shown in FIG. 4. In FIGS. 5A-5B, the wedges 6806a, 6806b each have an irregular quadrilateral or tetragon shape. If the individual shapes of the wedges 6806a, 6806b are laterally combined, the combination has a square shape. As described above, the wedges 6806a, 6806b are configured to compress and acoustically couple the piezoelectric elements 6808a-6808f to an ultrasonic waveguide through the stud 6804.

The rightward facing sectional view of FIG. 5A is obtained by starting from the longitudinal axis passing through the center of the transducer assembly 6800 and continuing right in the direction of the corresponding arrow 5A, as depicted in FIG. 4. As can be seen in FIG. 5A, in one aspect, the first pair of shorting caps 6810a-6810c may be connected in an offset manner. Specifically, shorting cap 6810c may be connected to a pole of the ultrasonic signal generator on one end and to the activating electrode 6809b on the other end. Similarly, shorting cap 6810a may be connected to the activating electrode 6809b on one end and to the activating electrode 6809d on the other end. Shorting cap 6810b may be connected to the activating electrode 6809d on one end and to activating electrode 6809f on the other end. Accordingly, the shorting caps 6810a-6810c are configured to provide a safe means of closing the electrical circuit connecting the generator to the piezoelectric elements 6808a-6808f and electrodes 6809a-6809g. As can be seen in FIG. 5A, the shorting cap 6810a is positioned on the upper side of the transducer assembly 6800 while the shorting caps 6810b-6810c are positioned on the lower side of the transducer assembly 6800.

The leftward facing sectional view of FIG. 5B is obtained by starting from the longitudinal axis passing through the center of the transducer assembly 6800 and continuing left in the direction of the corresponding arrow 5B, as depicted in FIG. 4. In another aspect, as can be seen in FIG. 5B, the second pair of shorting caps 6810a-6810c may be connected in an opposing offset manner. Specifically, shorting cap 6810g may be connected to a pole of the ultrasonic signal generator on one end (opposing the pole that shorting cap 6810c is connected to) and to activating electrode 6809a on the other end. Similarly, shorting cap 6810d may be connected to the activating electrode 6809a on one end and to activating electrode 6809c on the other end. Shorting cap 6810f may be connected to activating electrode 6809c on one end and to activating electrode 6809e on the other end. Shorting cap 6810e may be connected to activating electrode 6809e on one end and to activating electrode 6809g on the other end. Accordingly, the shorting caps 6810d-6810g also are configured to provide a safe means of closing the electrical circuit connecting the generator to the piezoelectric elements 6808a-6808f and electrodes 6809a-6809g. As can be seen in FIG. 5B, the shorting caps 6810g and 6810f are positioned on the lower side of the transducer assembly 6800 while the shorting caps 6810d-6810e are positioned on the upper side of the transducer assembly 6800.

Figure 5C:
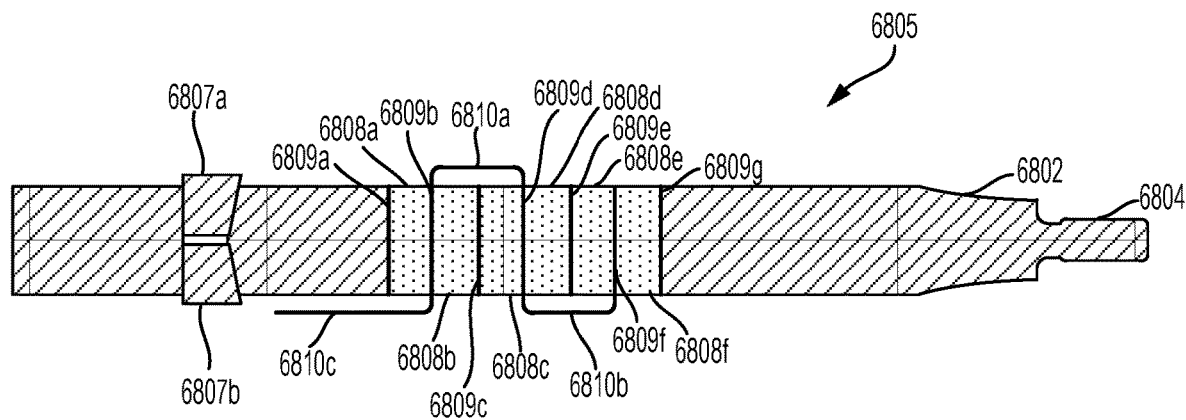
FIGS. 5C-5D illustrate cross section views of the ultrasonic transducer assembly 6805 employing another wedge configuration taken along similar section lines as shown in FIGS. 5A and 5B, according to one aspect of this disclosure.
Figure 5D:
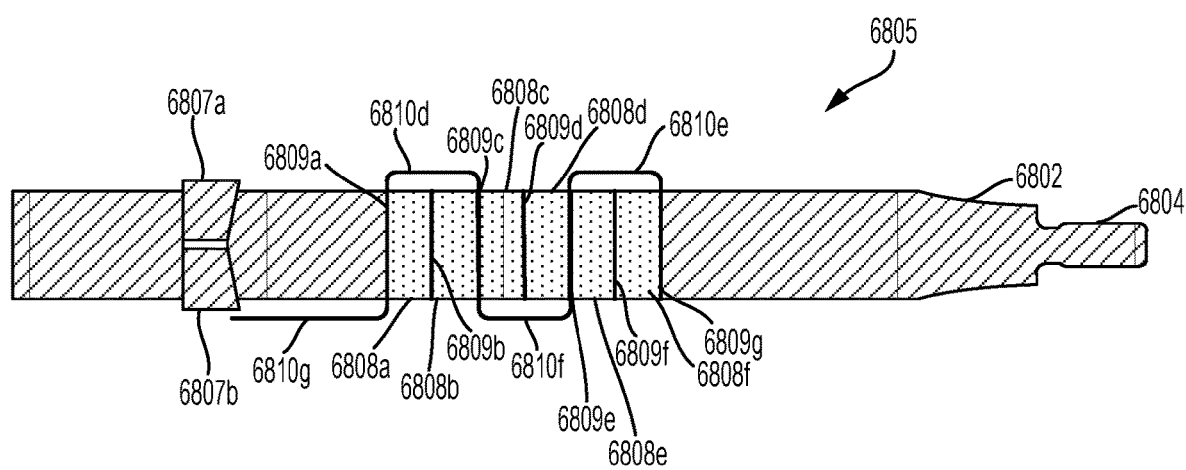

FIGS. 5C-5D illustrate cross section views of the ultrasonic transducer assembly 6805 employing another wedge configuration taken along similar section lines as shown in FIGS. 5A and 5B, according to one aspect of this disclosure. In FIGS. 5C-5D, the wedges 6807a, 6807b have a different irregular quadrilateral or tetragon shape than the shape of the wedges 6806a, 6806b in FIGS. 5A-5B. If the individual shapes of the wedges 6807a, 6807b are longitudinally combined, the combination has a square shape. As described above, the wedges 6807a, 6807b are configured to compress and acoustically couple the piezoelectric elements 6808a-6808f to an ultrasonic waveguide through the stud 6804. FIG. 5C depicts the same configuration of shorting caps 6810a-6810c as described in connection with FIG. 5A. Similarly, FIG. 5D depicts the same configuration of shorting caps 6810d-6810g as described in connection with FIG. 5B.

Figure 6:
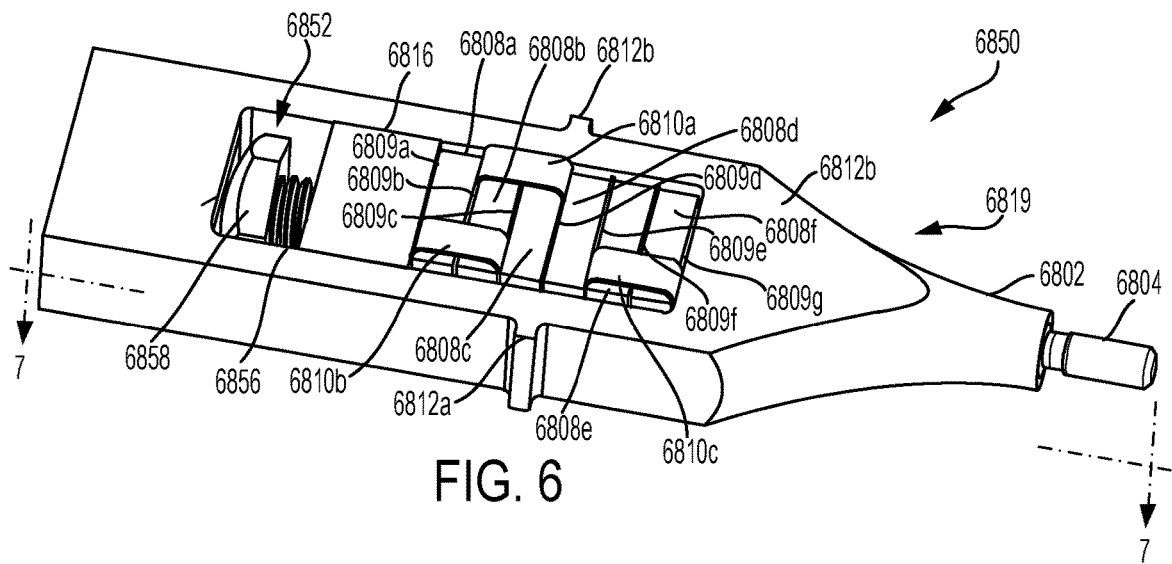
FIG. 6 is perspective view of an ultrasonic transducer assembly employing a screw to compress against the compression plate to compress and acoustically couple piezoelectric elements to an ultrasonic waveguide, according to one aspect of this disclosure.
Figure 7:
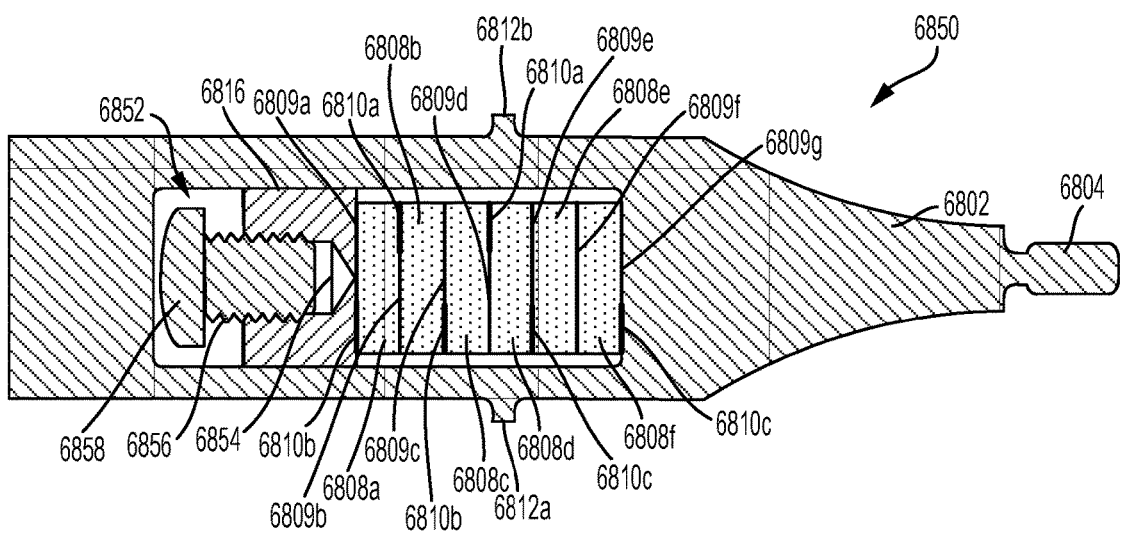
FIG. 7 is a section view of the of the ultrasonic transducer assembly shown in FIG. 6 taken along section 7-7 as shown in FIG. 6.
Figure 8:
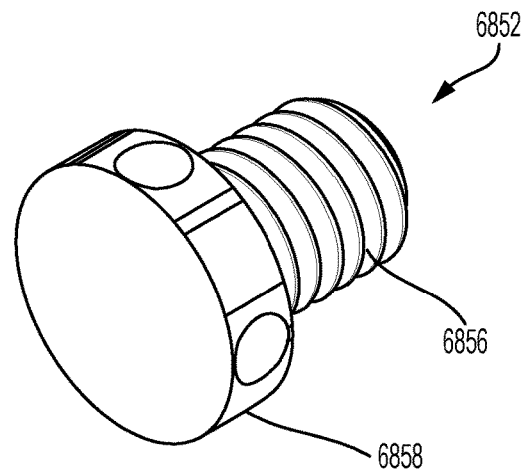
FIG. 8 is a perspective view of the screw, according to one aspect of this disclosure.

FIG. 6 is a perspective view of an ultrasonic transducer assembly 6850 similar to the ultrasonic surgical instrument 6800 according to one aspect of this disclosure, except that the transducer assembly 6850 comprises a transducer 6819 employing a screw 6852 to compress against the compression plate 6816 to compress and acoustically couple the piezoelectric elements 6808a-6808f to an ultrasonic waveguide. FIG. 7 is a section view of the ultrasonic transducer assembly 6850 taken along section line 7-7 as shown in FIG. 6, according to one aspect of this disclosure. With reference now to FIGS. 6-7, in one aspect, no wedges are used in the ultrasonic surgical instrument 6850, as shown in the perspective view of FIG. 6. Instead, the screw 6852 may be fastened into the compression plate 6816 to apply a compressive force against the compression plate 6816, such as by threading the pointed point or tip 6854 (and a proximal portion of the thread) of the screw 6852 distally into the compression plate 6816. As can be seen in the sectional view of FIG. 7, the pointed tip 6854 of the screw 6852 is in contact with the most proximal of the piezoelectric elements 6808. A distal portion of the thread 6856 and the head 6858 of the screw 6852 extend distally from the compression plate 6816. Advantages of this screw configuration include avoiding the use of a central bolt for compression and coupling and the ability to tune the acoustic assembly of the transducer assembly 6850 by modulating the tension in the transducer 6819 with the screw 6852. Compared to a transducer assembly with a central bolt, the transducer assembly 6850 with the screw 6852 is easier to machine because the distal portion of the thread 6856 of the screw 6852 is simply fastened into the compression plate 6816. FIG. 8 is a perspective view of the screw 6852, according to one aspect of this disclosure.

Figure 9:
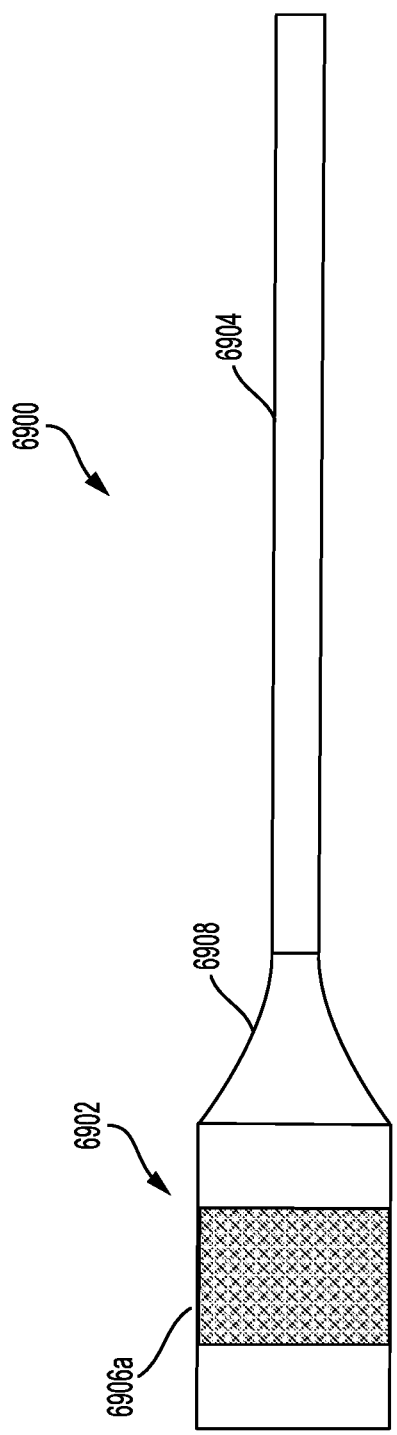
FIG. 9 illustrates an ultrasonic surgical instrument configured to operate in a D31 mode of operation, according to one aspect of this disclosure.
Figure 10:
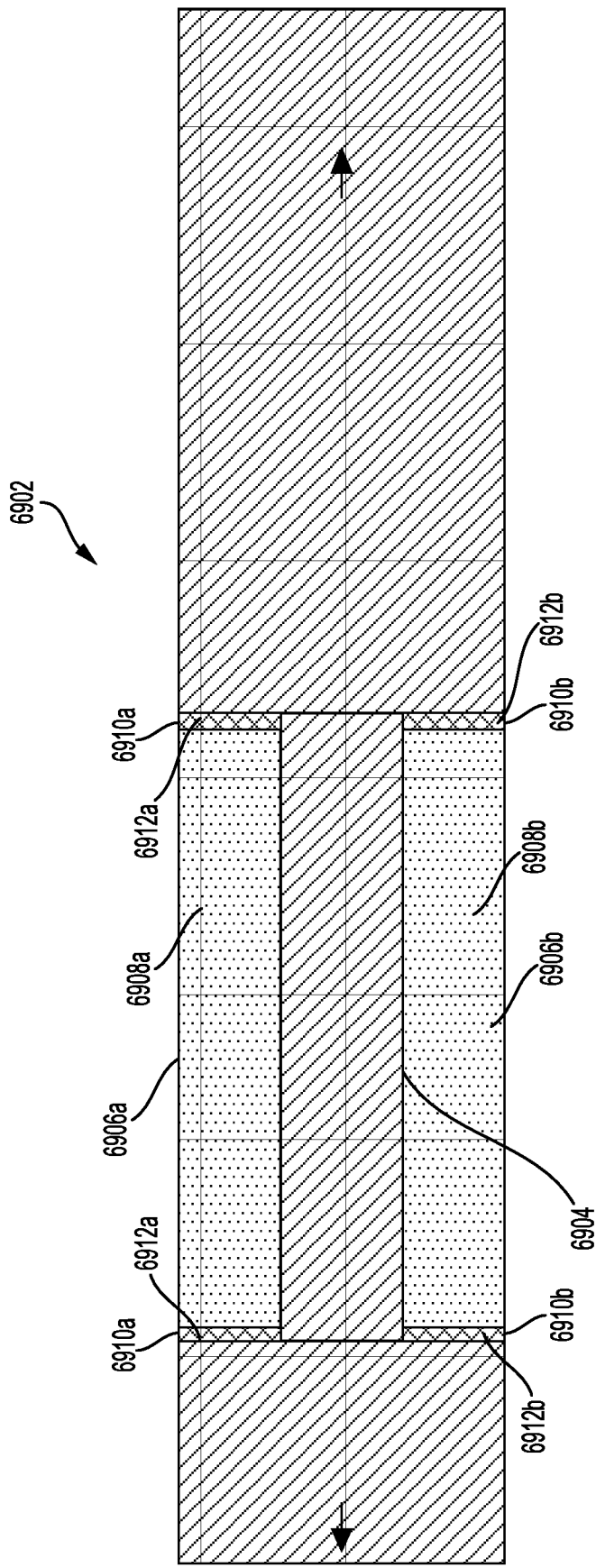
FIG. 10 is a section view of the transducer assembly comprising a first piezoelectric element positioned on a first side of the waveguide and a second piezoelectric element positioned on a second opposing side of the waveguide, according to one aspect of this disclosure.

FIG. 9 illustrates an ultrasonic surgical instrument 6900 configured to operate in a D31 mode of operation, according to one aspect of this disclosure. The ultrasonic surgical instrument 6900 comprises a transducer assembly 6902 and an ultrasonic waveguide 6904. The transducer assembly 6902 includes a horn shaped portion 6908, piezoelectric elements 6906a, 6906b, and a threaded connection such as a stud 6804 to connect to the ultrasonic waveguide 6904. As illustrated in FIG. 10, the transducer assembly 6902 is configured to create a strong mechanical bond between each of the piezoelectric elements 6906a, 6906b and the waveguide 6904. FIG. 10 is a section view of the transducer assembly 6902 comprising a first piezoelectric element 6906a positioned on a first side of the waveguide 6904 and a second piezoelectric element 6906b positioned on a second opposing side (opposing the first side) of the waveguide 6904, according to one aspect of this disclosure. In one aspect, the waveguide 6904 includes a first and second interior recess 6908a, 6908b for insertion of the piezoelectric elements 6906a, 6906b, respectively. As illustrated in FIG. 10, the first interior recess 6908a may extend from an interior top surface into and the second interior recess 6908a may extend from an interior bottom surface into the waveguide 6904, respectively. The depths of the first and second recess 6908a, 6908b may each equal or substantially equal the heights of the piezoelectric elements 6906a, 6906b, respectively.

Accordingly, when the piezoelectric elements 6906a, 6906b are inserted into the recesses 6908a, 6908b, the piezoelectric elements 6906a, 6906b can be flush (i.e., level or substantially level) with the waveguide 6904. In other words, the highest point or portion of the piezoelectric element 6906a is aligned with the exterior top surface of the waveguide 6904. Similarly, the lowest point or portion of the piezoelectric elements 6906b is aligned with the exterior bottom surface of the waveguide 6904. Thus, neither of the piezoelectric elements 6906a, 6906b protrudes beyond the exterior top or bottom surface of the waveguide 6904. In another aspect, the length of each interior recess 6908a, 6908b is greater than the respective length of each of the piezoelectric elements 6906a, 6906b. Consequently, when the piezoelectric elements 6906a, 6906b are inserted into the respective interior recesses 6908a, 6908b, there are proximal and distal gap portions 6910a, 6910b of the recesses 6908a, 6908b. Bonding material (e.g., conductive adhesive) such as cured epoxy adhesive 6912a, 6912b is applied to each of the gap portions 6910a, 6910b.

Consequently, a strong and durable mechanical bond between each of the piezoelectric elements 6906a, 6906b and the waveguide 6904 is created because of a lower risk of epoxy adhesive 6912a, 6912b bond failure during operation of the transducer 6902. Specifically, the tensile strength of epoxy may be substantially greater than the shear strength of epoxy. During operation of the transducer 6902, the epoxy adhesive 6912a, 6912b may experience a high extent of shear loading which can cause the bonds of the epoxy adhesive 6912a, 6912b to fail via delamination, for example. However, as shown in the transducer assembly 6902 of FIG. 10, the epoxy adhesive 6912a, 6912b is loaded in a tensile configuration, which may result in a lower rate of bond failure. Therefore, advantages of the transducer configuration of FIG. 10 include a strong mechanical coupling between each of the piezoelectric elements 6906a, 6906b and the waveguide 6904. In another aspect, no bonding material might be applied to the surfaces of the piezoelectric elements 6906a, 6906b that contact the waveguide 6904.

Figure 11:
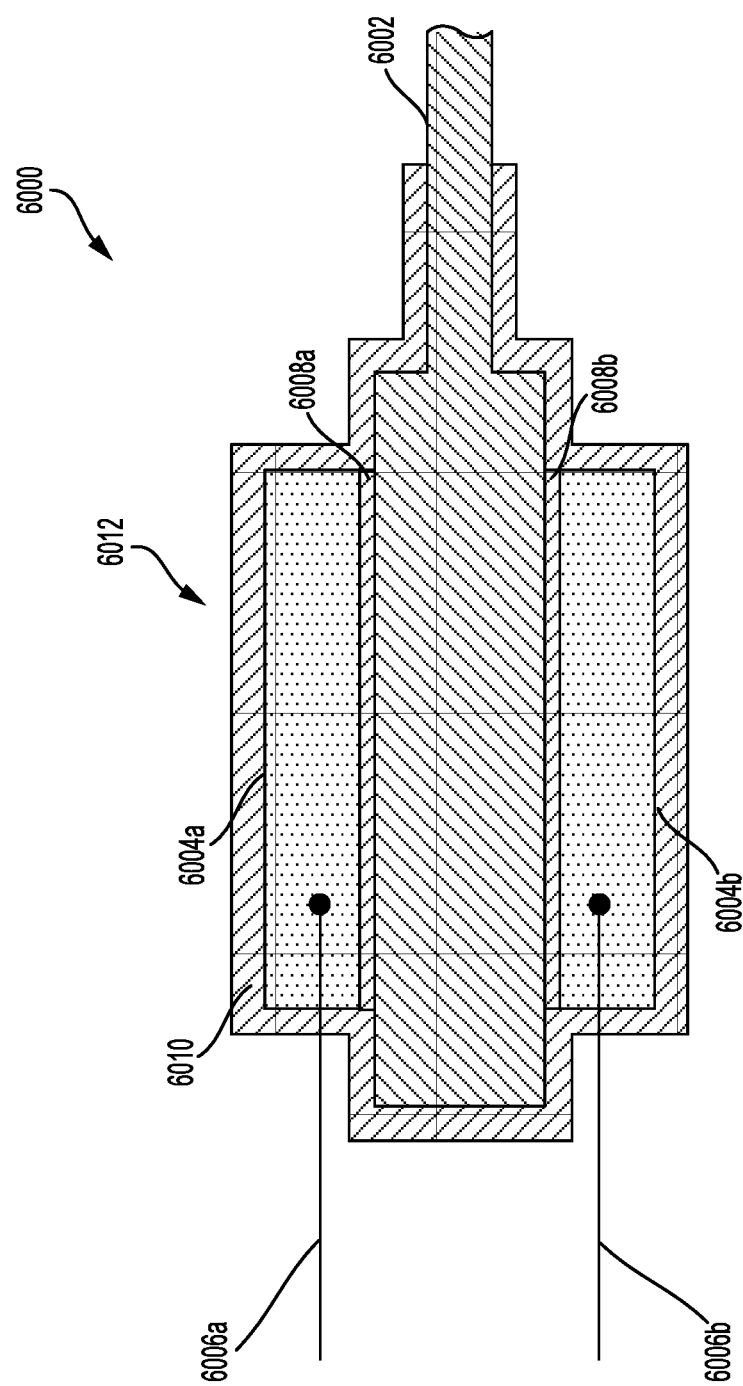
FIG. 11 is a section view of an ultrasonic surgical instrument configured to operate in a D31 mode of operation, according to one aspect of this disclosure.

The D31 architecture 250 according to one aspect of this disclosure employs a variety of different techniques to electrically and thermally couple the piezoelectric elements 254a, 254b to the ultrasonic waveguide 252. These techniques are disclosed hereinbelow. FIG. 11 is a section view of an ultrasonic surgical instrument 6000 configured to operate in a D31 mode of operation, according to one aspect of this disclosure. The ultrasonic surgical instrument 6000 includes an ultrasonic transducer 6012 attached to an ultrasonic waveguide 6014 by a bonding material. The ultrasonic surgical instrument 6000 comprises the waveguide 6014, first and second piezoelectric elements 6004a, 6004b, first and second electrically conductive elements 6006a, 6006b, and an overmolded housing 6010. Components of the transducer 6012 include the first and second piezoelectric elements 6004a, 6004b attached to opposing sides of the waveguide 6014 by a bonding material, such as first and second conductive adhesive 6008a, 6008b. The first and second conductive adhesive 6008a, 6008b can be a conductive epoxy adhesive, for example.

As shown in FIG. 11, the lower surface of the piezoelectric element 6004a is coupled to waveguide 6014 by the conductive adhesive 6008a and the upper surface of the piezoelectric element 6004b is coupled to waveguide 6014 by the conductive adhesive 6008b. The lower and upper surface may be opposing. The overmolded housing 6010 can be formed by a suitable overmolding process such a low pressure, hot melt adhesive molding process. For example, the TECHNOMELT® molding process of Henkel Electronic Materials LLC of Irvine, Calif., can be used with a suitable polyamide or polyolefin to form the overmolded housing 6010. The overmolded housing 6010 is configured to encompass at least a portion of the ultrasonic surgical instrument 6000. In one aspect, the overmolded housing 6010 encompasses the transducer 6012 and a proximal portion of the waveguide 6014. By encompassing the first and second piezoelectric elements 6004a, 6004b and a proximal portion of the waveguide 6014, the overmolded housing 6010 can ensure a durable and consistent attachment or coupling between the piezoelectric elements 6004a, 6004b and waveguide 6014.

Specifically, the overmolded housing 6010 may be configured to compress the first and second piezoelectric elements 6004a, 6004b against the waveguide 6014 or retain the elements 6004a, 6004b and waveguide 6014 in a friction fit. Additionally, the overmolded housing 6010 may be formed to include nonmolded portions for electrically conductive elements 6006a, 6006b to protrude from the overmolded housing 6010. As illustrated in FIG. 11, the leads 6006a, 6006b protrude proximally from the housing 6014 to electrically couple the first and second piezoelectric elements 6004a, 6004b to an ultrasonic signal generator. In one aspect, the first and second piezoelectric elements 6004a, 6004b are electrically coupled to a positive pole of an ultrasonic signal generator. As shown in FIG. 11, the waveguide 6002 may taper distally. The piezoelectric elements 6004a, 6004b may be constructed of ceramic material, such as PZT. The electrically conductive elements 6006a, 6006b may be electrical connectors such as wires, leads, metal electrically conductive pads (e.g., Solder Mask Defined pad (SMD) or Non-Solder Mask Defined pad (NSMD)), or other suitable electrical connectors.

Figure 12:
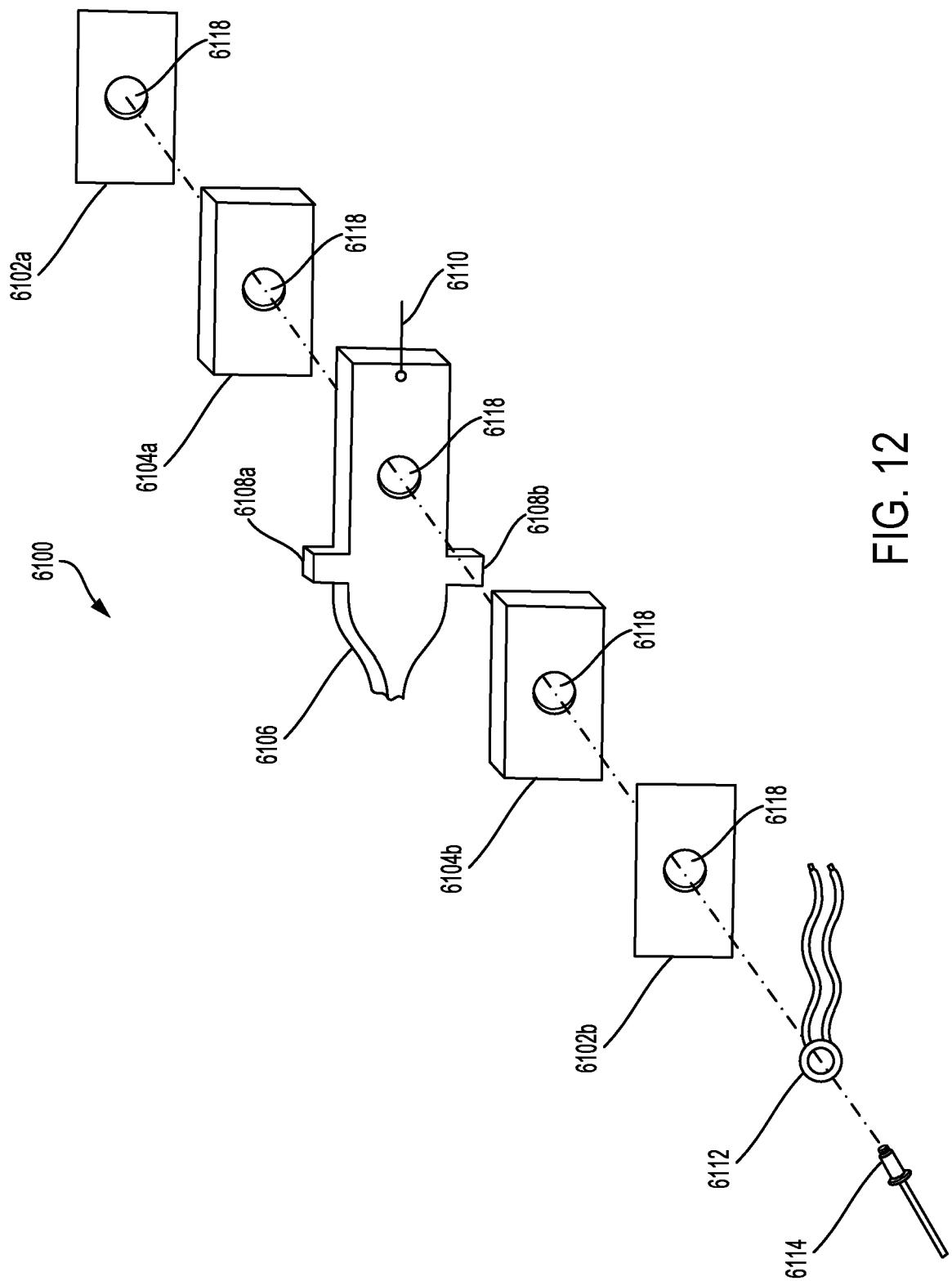
FIG. 12 is an exploded view of an ultrasonic surgical instrument configured to operate in a D31 mode of operation, according to one aspect of this disclosure.

FIG. 12 is an exploded view of an ultrasonic surgical instrument 6100 configured to operate in a D31 mode of operation, according to one aspect of this disclosure. The ultrasonic surgical instrument 6100 comprises a plurality of plate components, including first and second electrode plates 6102a, 6102b, first and second piezoelectric plates 6104a, 6104b, transducer base plate 6106 (e.g., a transducer mounting portion), electrically conductive element such as wire loop 6112, and a pop rivet 6114. In one aspect, each of the plates 6102a, 6102b, 6104a, 6104b, 6106 each comprise a grooved receiving aperture 6118, which may be formed by a suitable machining process. Each of the grooved receiving apertures 6118 may be configured to receive wire loop 6112 in order to electrically couple the plates 6102a, 6102b, 6104a, 6104b, 6106. In particular, when combined with the pop rivet 6114, the wire loop 6112 may be coupled to a positive pole of a voltage or energy source (e.g., an ultrasonic signal generator). The transducer base plate 6106 may act as electrical ground for the current flowing through the wire loop 6112. A connection to electrical ground can be made through a ground wire 6110 of the transducer base plate 6106.

In another aspect, the ground wire 6110 is soldered, mechanically looped, or otherwise coupled via a suitable means to the transducer base plate 6106. Aside from the grooved receiving aperture 6118 and ground wire 6118, the transducer base plate 6106 comprises flanges 6108a, 6108b, which may be configured to be received within a retainer of a housing (not shown) of the ultrasonic surgical instrument 6100 for secure attachment of the transducer base plate 6106 to the housing. In another aspect, the pop rivet 6114 is configured to be inserted through the wire loop 6112 and each of the 6102a, 6102b, 6104a, 6104b, 6106 such that the pop rivet 6114 compresses the electrode plates 6102a, 6102b, which in turn compress the piezoelectric plates 6104a, 6104b. Unlike the aspect illustrated by FIG. 11, for example, the ultrasonic surgical instrument 6100 may not require the use of epoxy for electrical coupling. Instead, the pop rivet 6114 provides compression through the electrode plates 6102a, 6102b to electrically couple the piezoelectric plates 6104a, 6104b to a waveguide of the ultrasonic surgical instrument 6100. Advantages of the pop rivet 6114 configuration may include decreased assembly time, improved electrical coupling (based on the provided compression), and reduced cost (e.g., no epoxy is necessary).

Figure 13A:
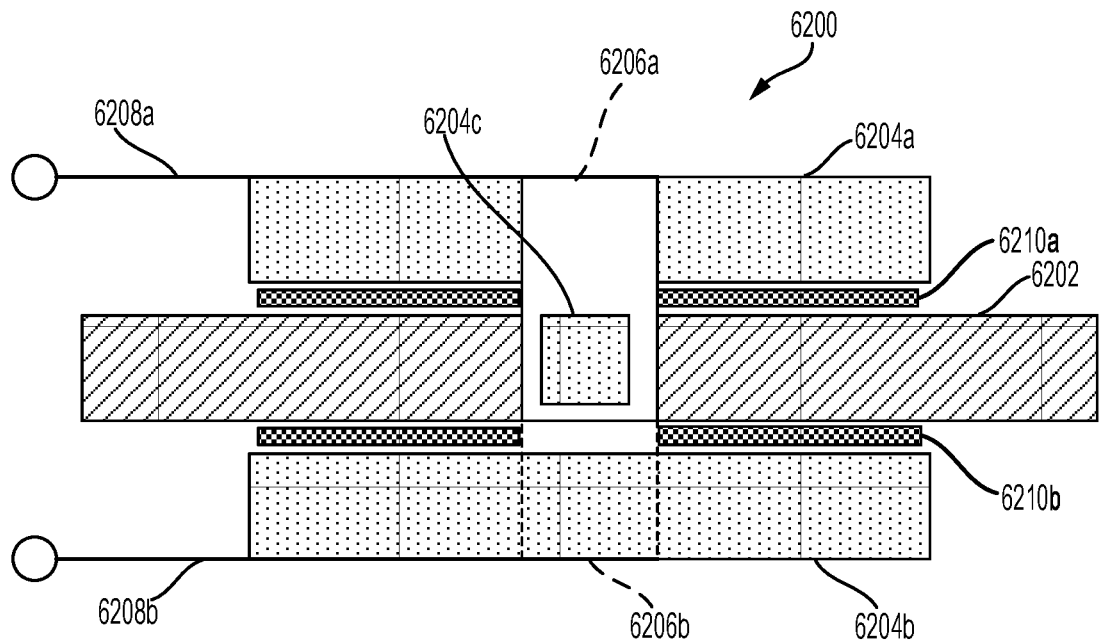
FIG. 13A is a side view of an ultrasonic surgical instrument configured to operate in a D31 mode of operation, according to one aspect of this disclosure.

FIG. 13A is a side view of an ultrasonic surgical instrument 6200 configured to operate in a D31 mode of operation, according to one aspect of this disclosure. The ultrasonic surgical instrument 6200 comprises an ultrasonic waveguide 6202, piezoelectric elements 6204a, 6204b, 6204c (shown in phantom), and electrode shims 6206a, 6206b. The ultrasonic waveguide 6202 comprises a recessed or "cut out" portion in which the piezoelectric element 6204c may be inserted. Piezoelectric element 6204c can have a smaller surface area than piezoelectric elements 6204a, 6204b. In one aspect, the electrode shims 6206a, 6206b are flat electrodes which are configured to electrically couple piezoelectric elements 6204a, 6204b, 6204c to each other and to a voltage or energy source (e.g., an ultrasonic signal generator). The electrode shim 6206a may include three portions which each compress against a surface of the piezoelectric element 6204a. For example, as shown in FIG. 13A, a portion of the electrode shim 6206a is wrapped into (i.e., extends in a sideways direction toward an interior portion of the ultrasonic surgical instrument 6200 to contact) the piezoelectric element 6204c inserted inside the recessed portion of the waveguide 6202 for electrical coupling of the piezoelectric elements 6204a, 6204b, 6204c.

Additionally, as shown in phantom in FIG. 13A, the electrode shim 6206b is also wrapped into (i.e., extends in a sideways direction toward an interior portion of the ultrasonic surgical instrument 6200 to contact) the piezoelectric element 6204c or electrical coupling of the piezoelectric elements 6204a, 6204b, 6204c. The electrode shims 6206a, 6206b may be wrapped into the piezoelectric element 6204c in opposing directions. In another aspect, the piezoelectric element 6204a comprises a connection portion 6208a to electrically couple to a positive pole of the energy source and the piezoelectric element 6204b comprises a connection portion 6208b to electrically couple to a negative pole of the energy source. Accordingly, current may flow through the electrical connection portions 6208a, 6208b through the piezoelectric elements 6204a, 6204b, 6204c and the ultrasonic waveguide 6202, with the ultrasonic waveguide 6202 as electrical ground.

Figure 13B:
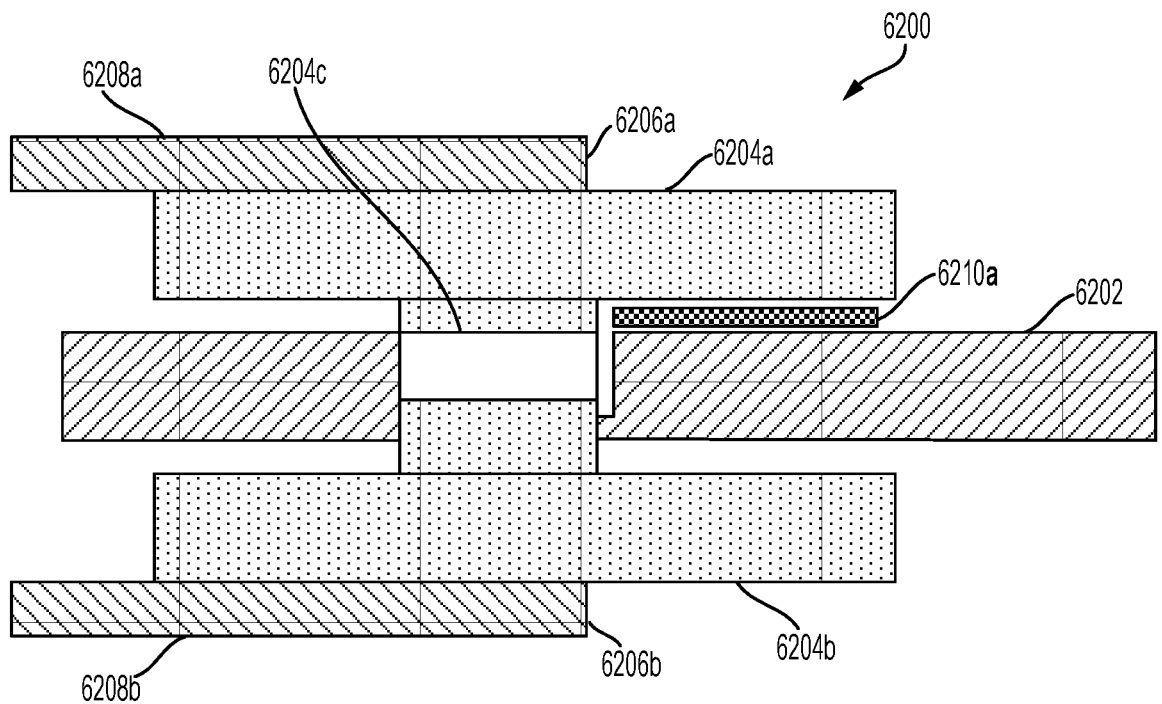
FIG. 13B is a cross sectional view of a side of the ultrasonic surgical instrument shown in FIG. 13A, according to one aspect of this disclosure.
Figure 14:
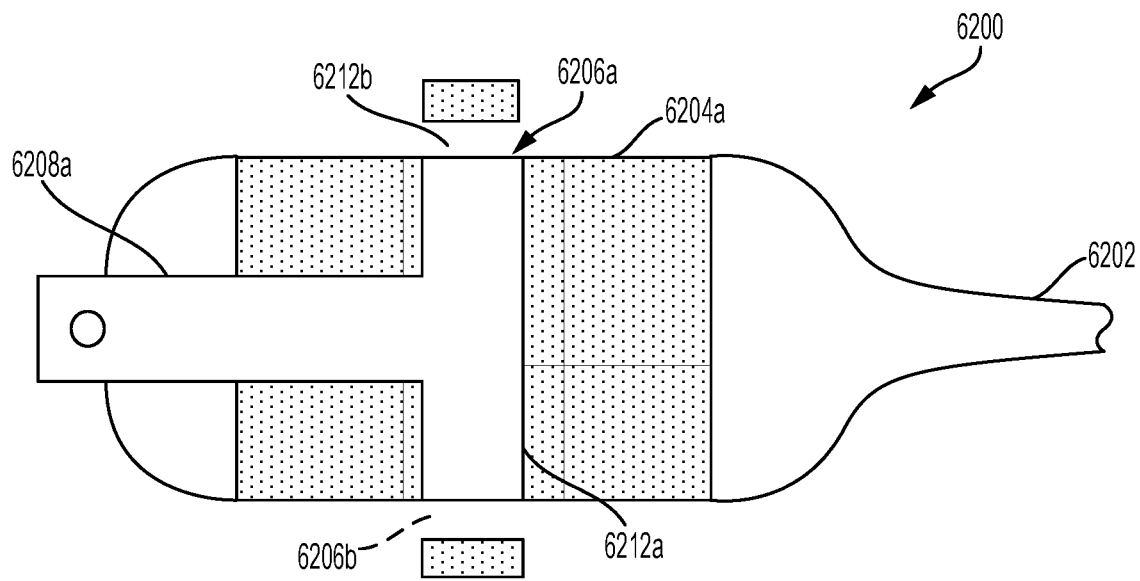
FIG. 14 is a top view of the ultrasonic surgical instrument shown in FIG. 13A, according to one aspect of this disclosure.

FIG. 13B is a cross sectional view of a side of the ultrasonic surgical instrument 6200, according to one aspect of this disclosure. As can be seen in FIG. 13B, an end of each of the electrode shims 6206a, 6206b is in contact with the piezoelectric element 6204c. Referring now to both FIGS. 13A and 13B, electrical insulation such as plastic or polyamide insulators 6210a, 6210b may be used to reduce or prevent the risk of electrical shorting. The insulator 6210a, 6210b may be positioned on either the electrode shims 6206a, 6206b or the waveguide 6202 such that current may flow through only a portion of the area located between one of the piezoelectric elements 6204a, 6204b and the waveguide 6202. In another aspect, similar to the piezoelectric elements 6004a, 6004b, the piezoelectric elements 6204a, 6204b can be attached to opposing sides of the waveguide 6202 by a bonding material, such as conductive epoxy adhesive. FIG. 14 is a top view of the ultrasonic surgical instrument 6200, according to one aspect of this disclosure.

Figure 15:
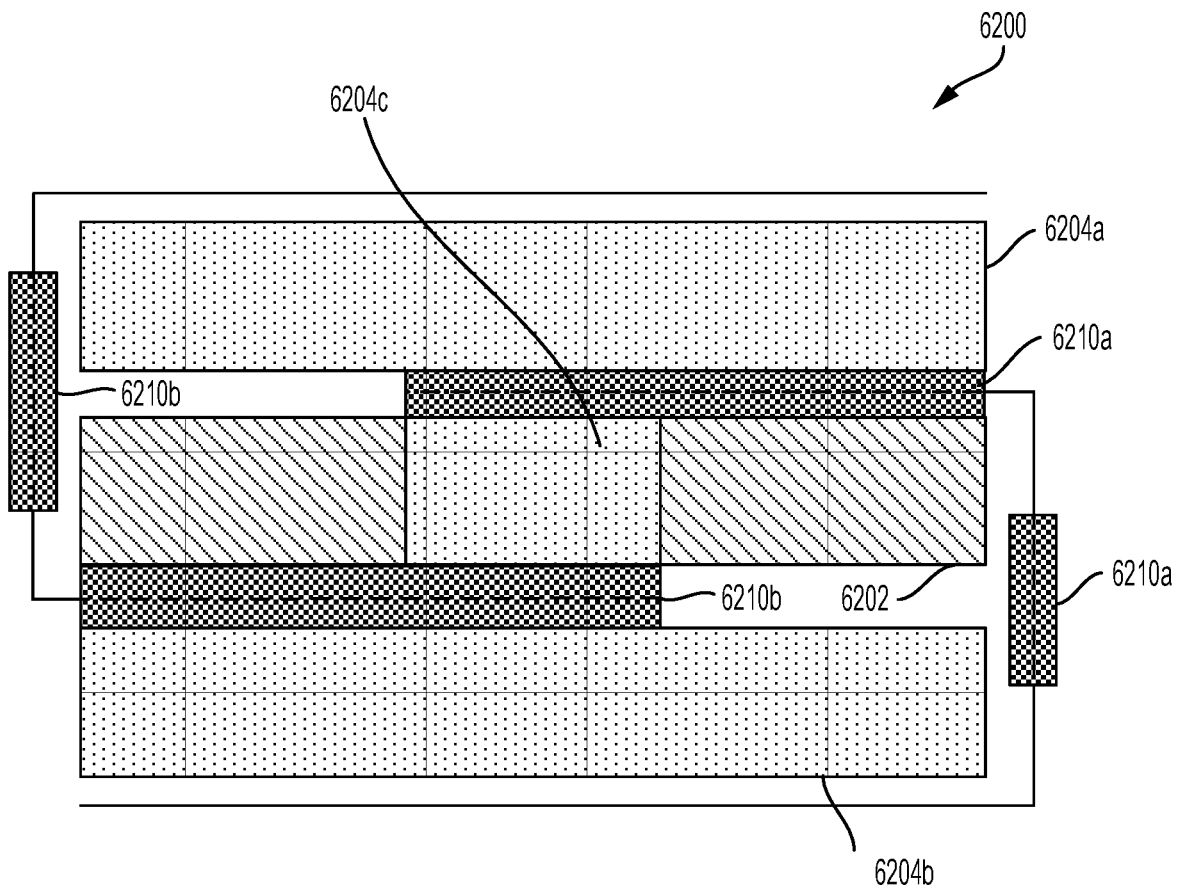
FIG. 15 is a rear cross sectional view of the ultrasonic surgical instrument shown in FIG. 13A, according to one aspect of this disclosure.

In FIG. 14, only the piezoelectric element 6204a is visible. As shown in FIG. 14, the first portion 6212a of the electrode shim 6206a is positioned on or wrapped into the top surface of the piezoelectric element 6204a. The second portion 6212b of the electrode shim 6206a is positioned on a first side surface of the piezoelectric element 6204a. In one aspect, the second portion of the other electrode shim 6206b is positioned on a second side surface of the piezoelectric element 6204a. The first and second side surfaces of the piezoelectric element 6204a are opposing. The third portion (not shown) of the electrode shim 6206a extends sideways toward the interior of the ultrasonic surgical instrument 6200 such that the third portion contacts the piezoelectric element 6204c. A portion of each of the electrical insulators 6210a, 6210b located on opposing surfaces of the ultrasonic surgical instrument 6200 may be seen in the view of FIG. 14. FIG. 15 is a rear cross sectional view of the ultrasonic surgical instrument 6200, according to one aspect of this disclosure. As can be seen in FIG. 15, insulator 6210a may extend from a side surface of the piezoelectric elements 6204a, 6204b into an area between the waveguide 6202 and the piezoelectric element 6204b. Similarly, insulator 6210b may extend from a side surface of the piezoelectric elements 6204a, 6204b into an area between the waveguide 6202 and the piezoelectric element 6204a.

Figure 16A:
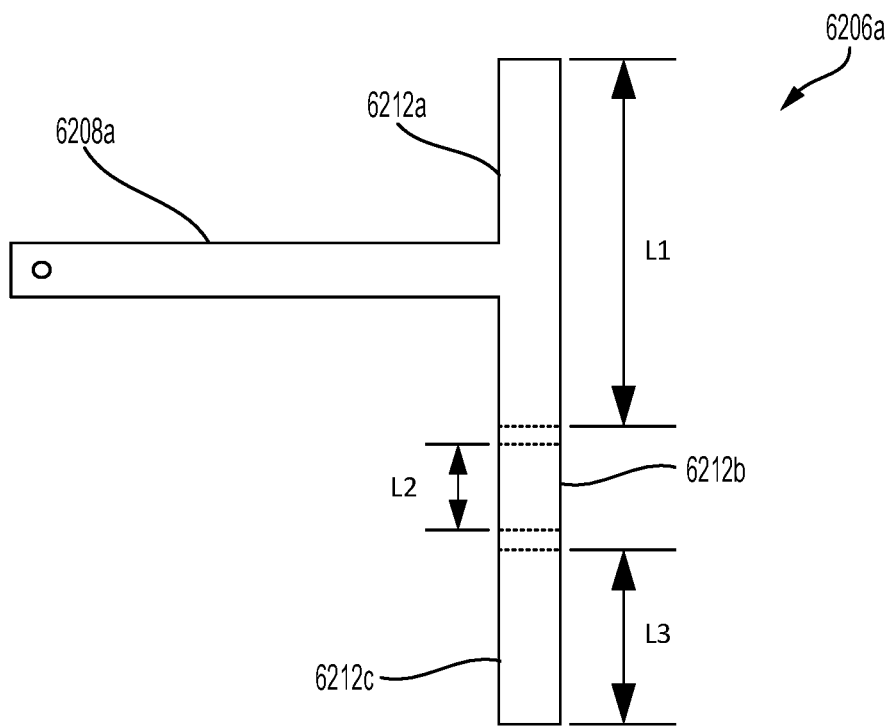
FIG. 16A is a plan view of an electrode shim in a flat configuration, according to one aspect of this disclosure.
Figure 16B:
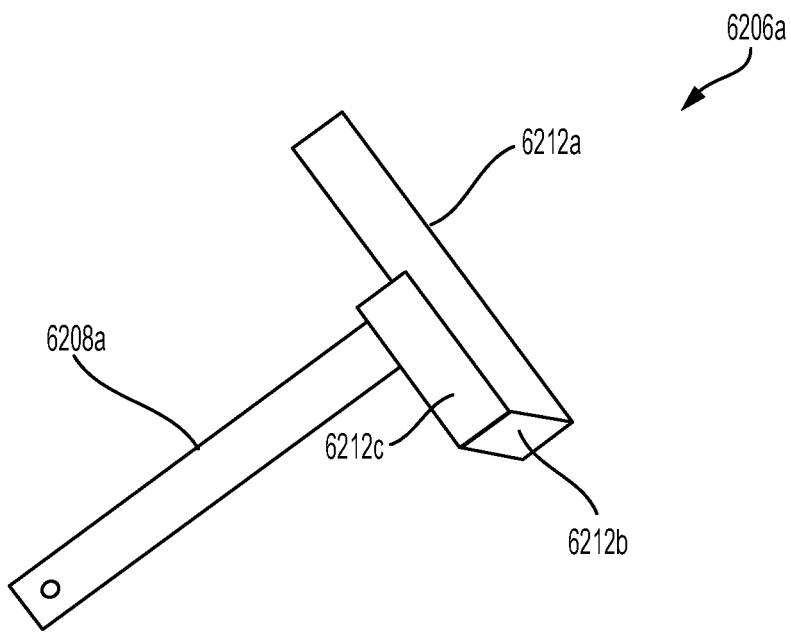
FIG. 16B is a perspective view of the electrode shim shown in FIG. 16A in a folded configuration, according to one aspect of this disclosure.

FIG. 16A is a plan view of an electrode shim 6206a in a flat configuration, according to one aspect of this disclosure. FIG. 16B is a perspective view of the electrode shim 6206a shown in FIG. 16A in a folded configuration, according to one aspect of this disclosure. As described above, the electrode shim 6206a comprises first, second and third portions 6212a, 6212b, 6212c. In addition, the electrode shim 6206a comprises the connection portion 6208a to connect to, for example, the positive pole of the energy source. According to one aspect of this disclosure, FIG. 16A illustrates the electrode shim 6206a, which may be manufactured as a flat electrode from a copper sheet and may be bent into three portions. The first portion 6212a can have the same or substantially the same length L1 as the waveguide 6202. The second portion 6212a can have the same or substantially the same length L2 as the waveguide 6202. The third portion 6212a can have two thirds the length L3 of the waveguide 6202. The electrode shim 6206b may be identical or substantially similar to the electrode shim 6206a, except that the electrode shim 6206b is oriented in an opposing direction. FIG. 16B is a perspective view of the electrode shim 6206a in a bent configuration, according to one aspect of this disclosure.

Figure 17A:
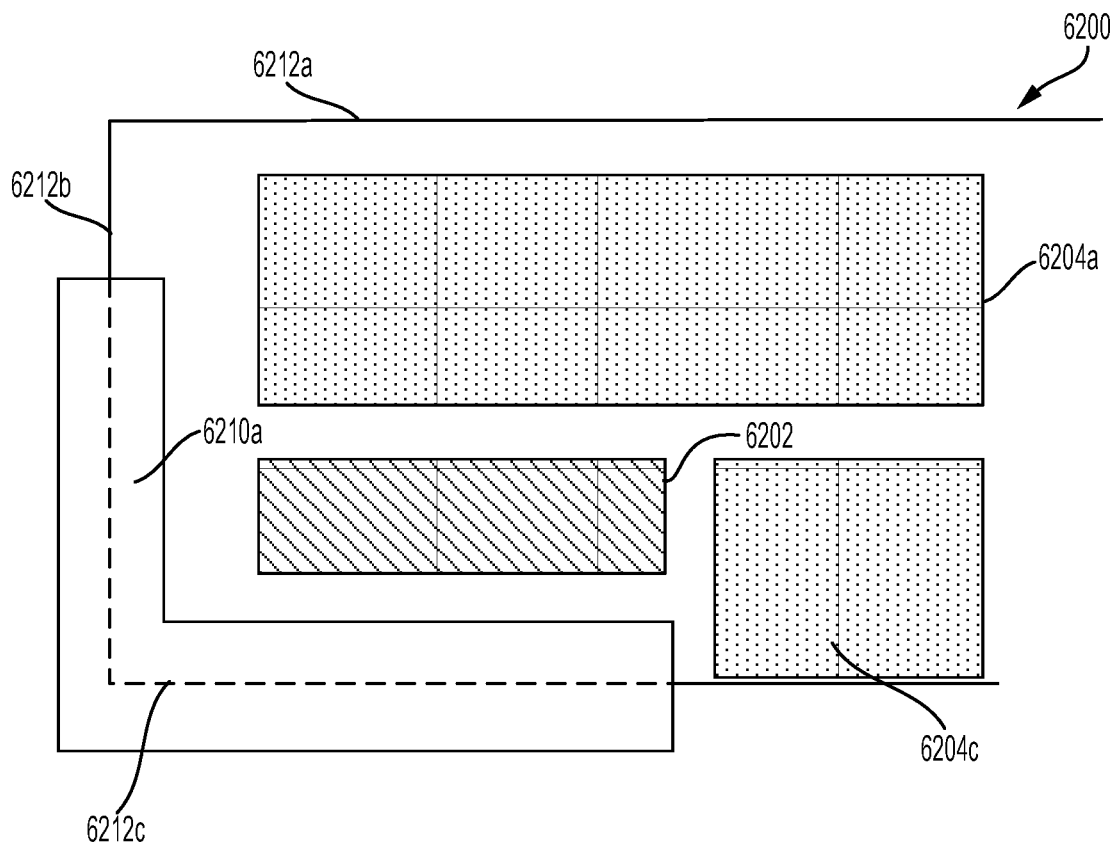
FIGS. 17A-17B are views of a portion of the ultrasonic surgical instrument shown in FIG. 13A, with polyimide film material coating as an insulator positioned on the electrode shim, according to one aspect of this disclosure.
Figure 17B:
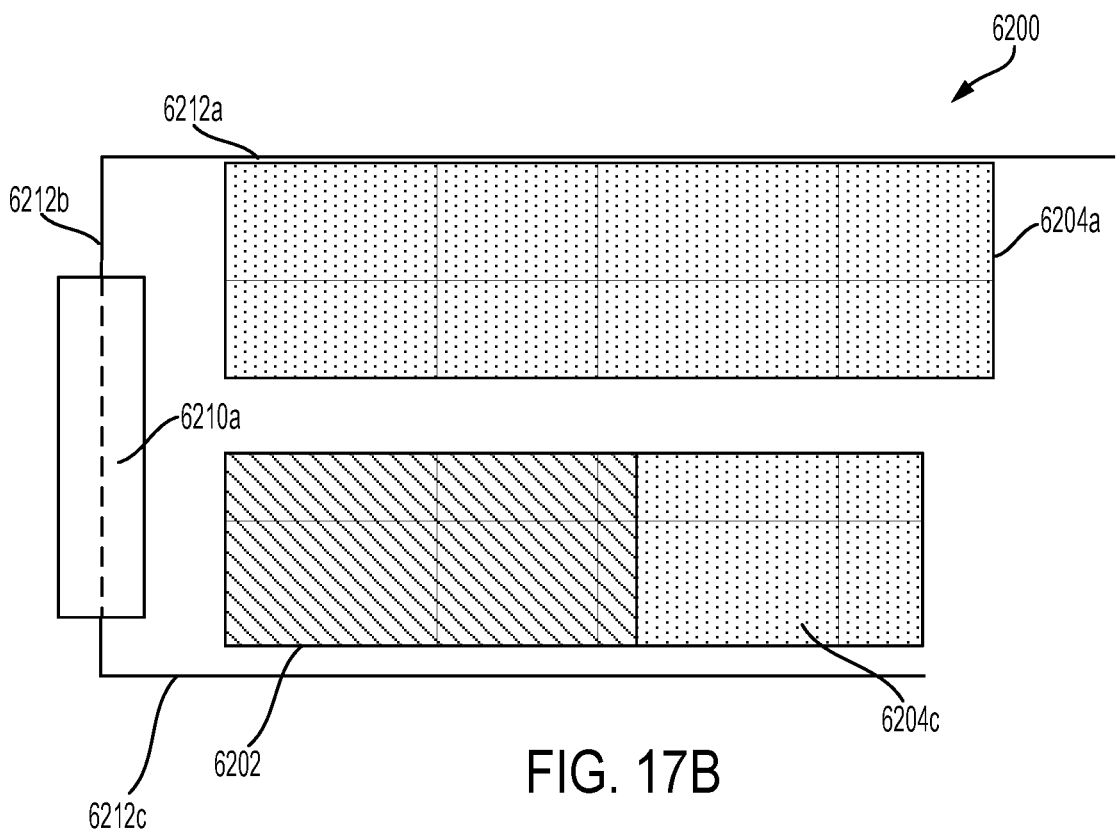

FIGS. 17A-17B are views of a portion of the ultrasonic surgical instrument 6200 with polyimide film material coating, such as Kapton® polyimide film available from E. I. du Pont de Nemours and Company of Wilmington, Del., as the insulator 6210a positioned on the electrode shim 6206a, according to one aspect of this disclosure. As shown in FIG. 17A, in one aspect, the Kapton insulator 6210a may be coated onto the bend between second and third portions 6212b, 6212c such that the Kapton insulator 6210a is positioned between the electrode shim 6206a and the waveguide 1602. In another aspect, as shown in FIG. 17B, the Kapton insulator 6210a may be applied on the second portion 6212b such that the Kapton insulator 6210a extends along the piezoelectric element 6204a and waveguide 6202.

Figure 18:
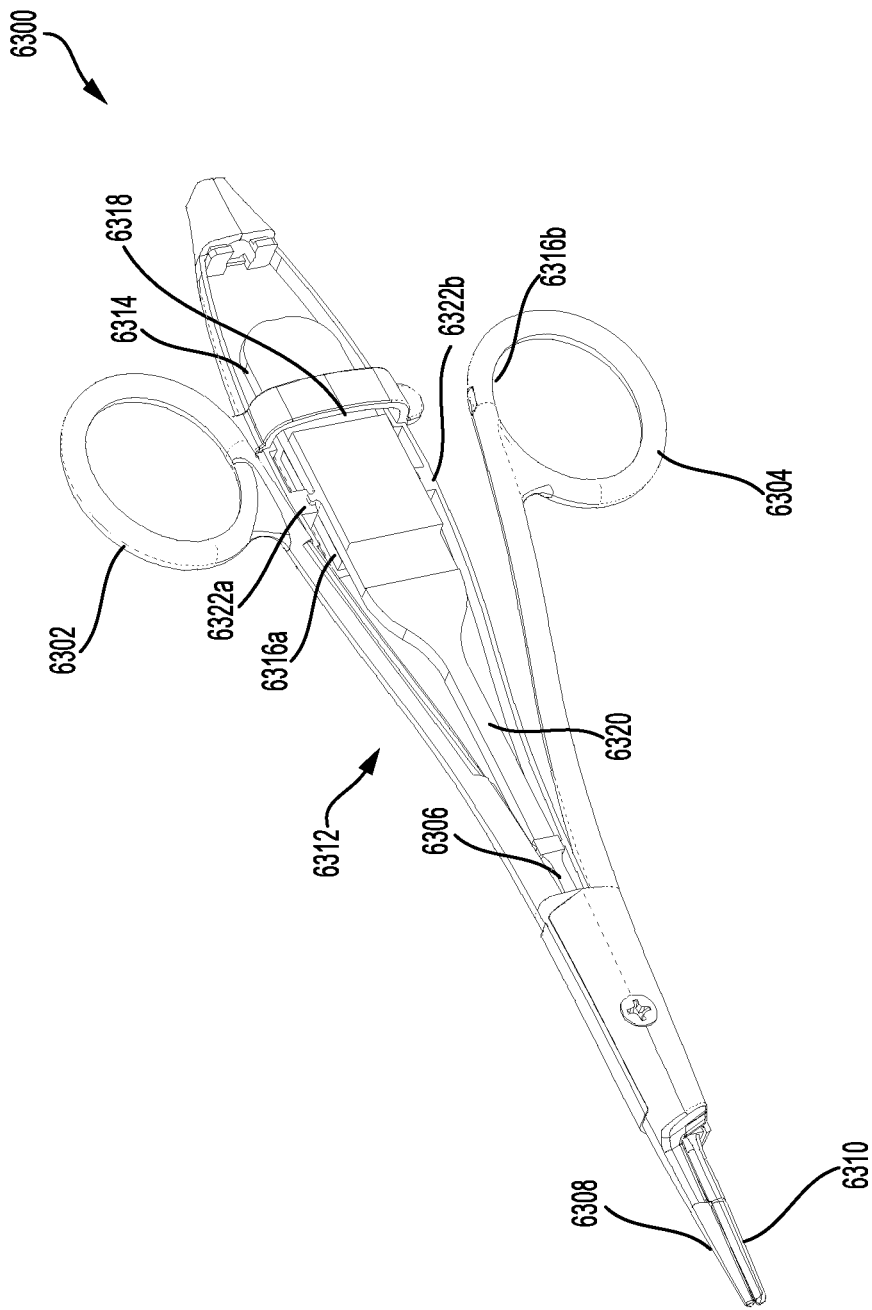
FIG. 18 is a perspective view of an ultrasonic surgical instrument, which is configured to operate in a D31 mode of operation, according to one aspect of this disclosure.

FIG. 18 is a perspective view of an ultrasonic surgical instrument 6300 (may be referred to as a pair of ultrasonic shears or forceps), which is configured to operate in a D31 mode of operation, according to one aspect of this disclosure. The shears 6300 comprise a first arm 6302 pivotably connected to a second arm 6304 by a fastener 6306. The first arm 6302 includes a jaw 6008 or clamp positioned at its distal end that is configured to cooperate with an end effector 9054 extending distally from the second arm 6304. Actuating the first arm 6302 in a first direction causes the jaw 6308 to pivot towards the end effector 6310 and actuating the first arm 6302 in a second direction causes the jaw 6308 to pivot away from the end effector 6310. In one aspect, the ultrasonic surgical instrument 6300 includes a transducer assembly 6312, such as the transducer assembly 6902. The transducer assembly 6312 comprises a housing 6314 enclosing the first and second piezoelectric elements 6316a, 6316b and an ultrasonic waveguide 6320. The first and second piezoelectric elements 6316a, 6316b are attached to opposite sides of the waveguide 6320 by a bonding material. The transducer 6318 includes the first and second piezoelectric elements 6316a, 6316b. The transducer assembly 6312 includes flanges 6322a, 6322b, which may be configured to be received within a retainer of the housing 6314 for secure attachment of the transducer 6318 to the housing 6314. The transducer assembly 6312 comprises a recessed receiving portion configured to receive an electrode for compressing the piezoelectric elements 6316a, 6316b.

Figure 19:
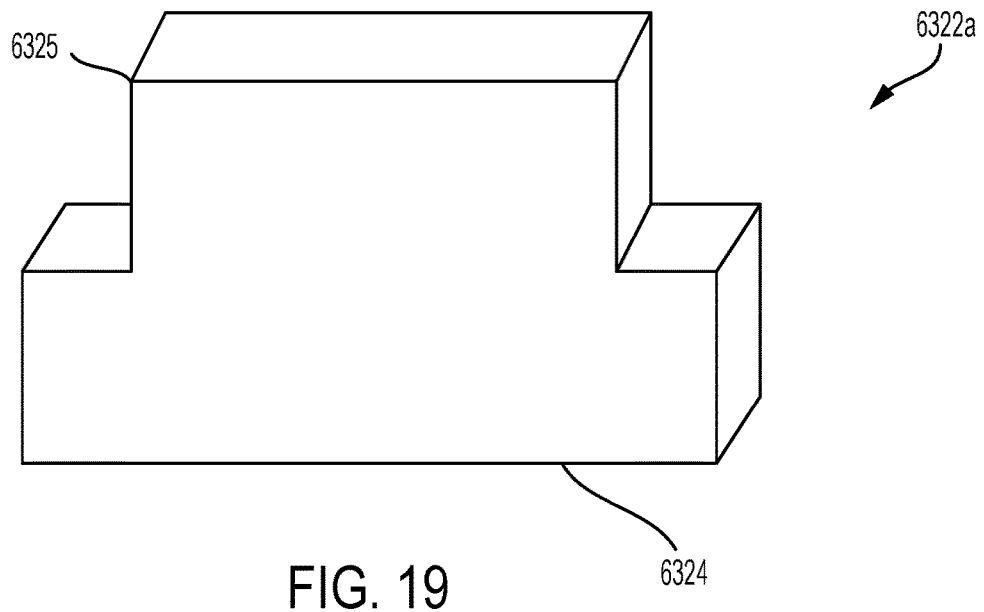
FIG. 19 is a perspective view of an electrode of the ultrasonic surgical instrument shown in FIG. 18, according to one aspect of this disclosure.
Figure 20:
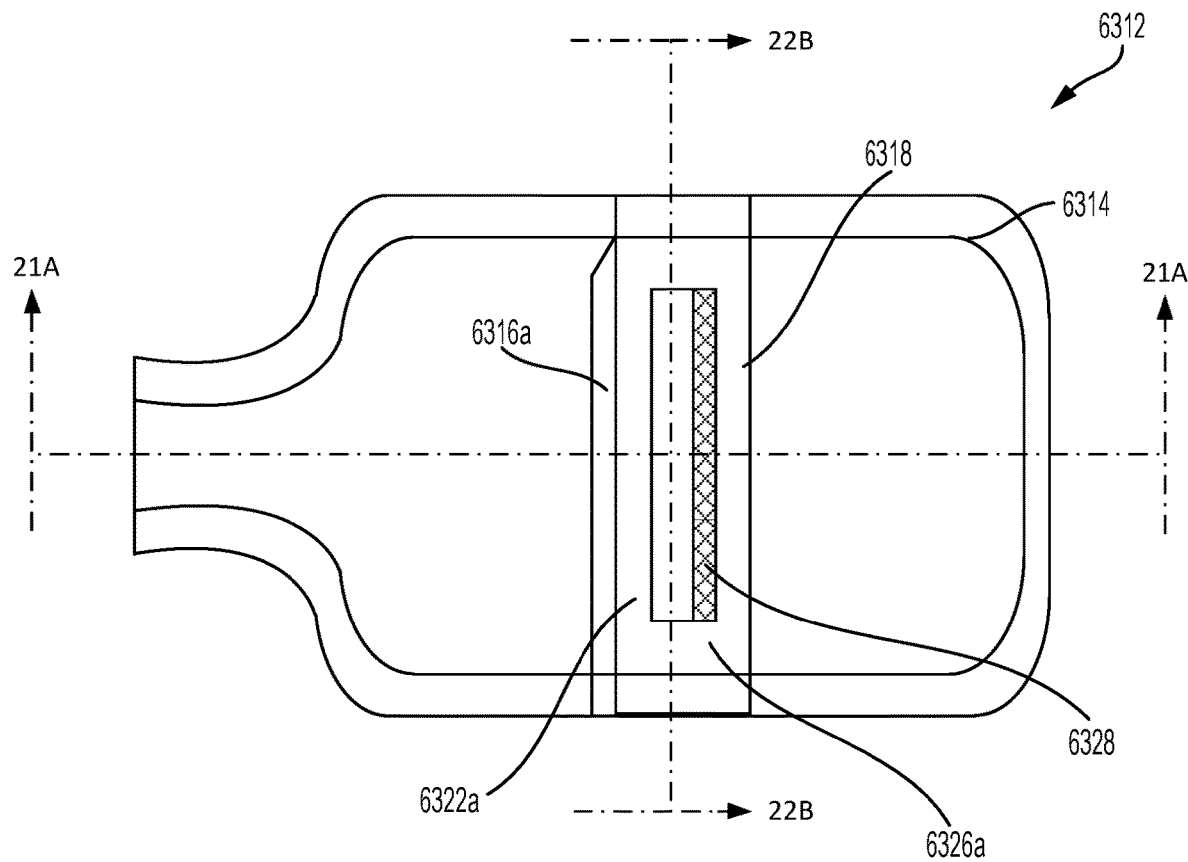
FIG. 20 is a plan view of the transducer assembly of the ultrasonic surgical instrument shown in FIG. 18 including a recessed receiving portion configured to receive an electrode, according to one aspect of this disclosure.

FIG. 19 is a perspective view of such an electrode 6322a of the ultrasonic surgical instrument 6300, according to one aspect of this disclosure. The electrode 6322a comprises a base portion 6324 and a protruding portion 6325. FIG. 20 is a plan view of the transducer assembly 6312 including a recessed receiving portion 6326a configured to receive an electrode such as the electrode 6322a, according to one aspect of this disclosure. The base of the recessed receiving portion 6326a and the electrode 6322a are visible in FIG. 20. As described below in further detail, the electrode 6322a may be positioned into a receiving area defined by the base via an interference or a geometrical fit. The electrode (e.g., conductive foam) 6322 is configured to compress the piezoelectric element 6316a to maintain electrical contact between the piezoelectric element 6316a and the waveguide 6320. In one aspect, a molded interconnect pad 6328 is used to electrically couple to an electrical connector (e.g., a wire) which is connected to an ultrasonic signal generator. In another aspect, conductive bonding material such as conductive grease adhesive is applied between the electrode 6322a and piezoelectric element 6316a for a stronger electrical connection.

Figure 21A:
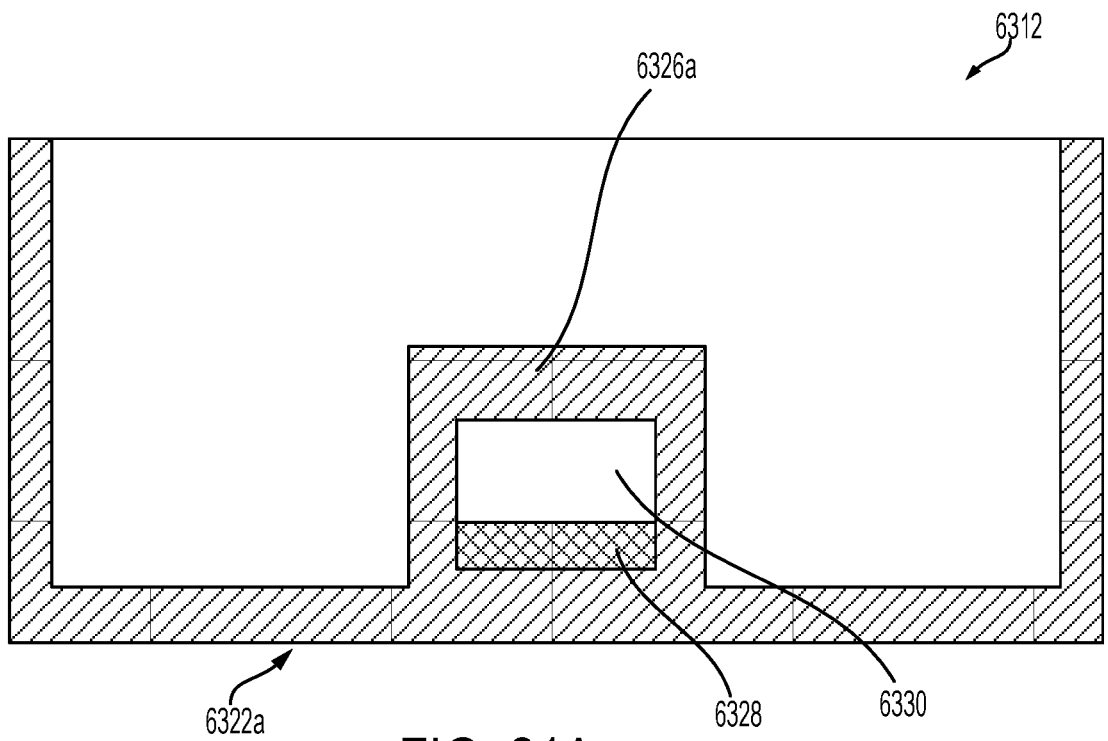
FIG. 21A is a longitudinal sectional view of the transducer assembly shown in FIG. 20, with a portion of the electrode, the molded interconnect pad, the receiving area, and a portion of the recessed receiving portion, according to one aspect of this disclosure.
Figure 21B:
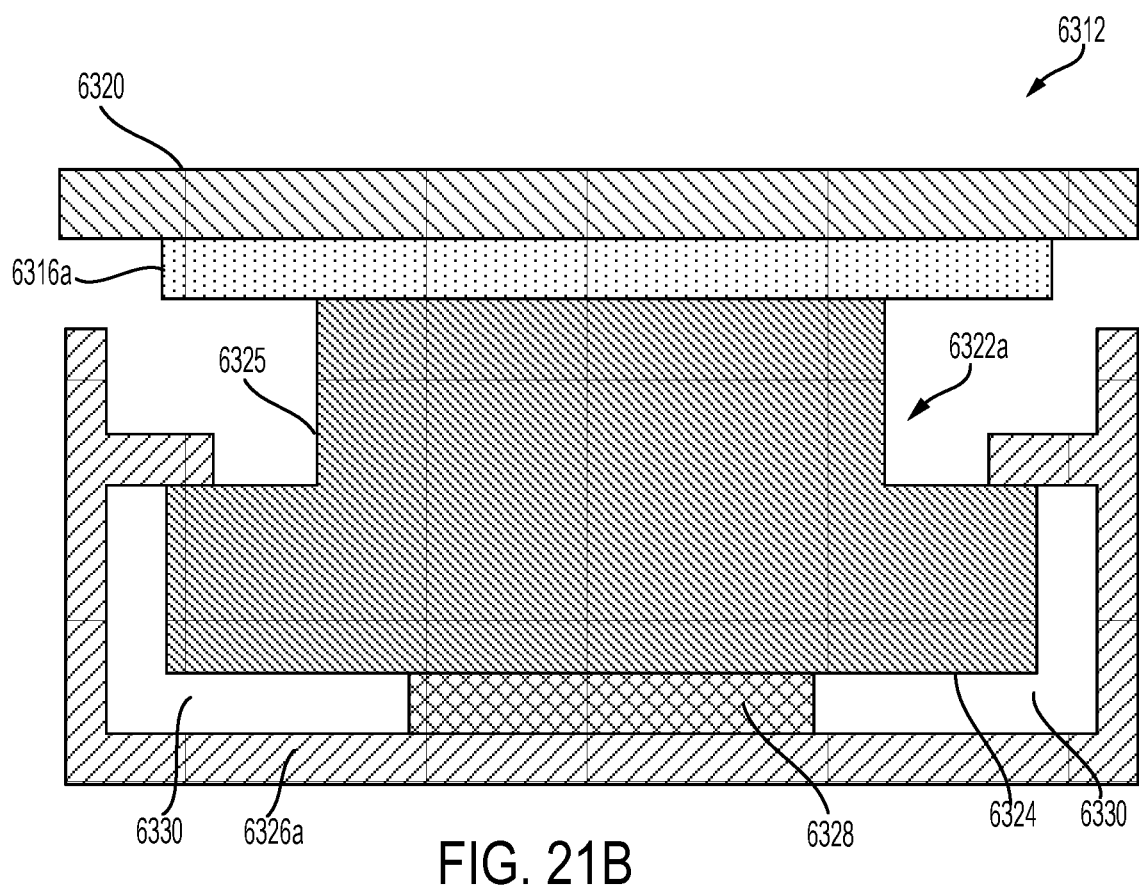
FIG. 21B is a lateral sectional view of the transducer assembly shown in FIG. 20, with a portion of the electrode, the molded interconnect pad, the receiving area, and the recessed receiving portion, according to one aspect of this disclosure.

FIG. 21A is a longitudinal sectional view of the transducer assembly 6312 which shows a portion of the electrode 6322a, the molded interconnect pad 6328, the receiving area 6330, and a portion of the recessed receiving portion 6326a, according to one aspect of this disclosure. The longitudinal sectional view is obtained based on a section starting from the axis AA and continuing in the direction of the depicted corresponding arrow. FIG. 21B is a lateral sectional view of the transducer assembly 6312 which shows a portion of the electrode 6322a, the molded interconnect pad 6328, the receiving area 6330, and the recessed receiving portion 6326a, according to one aspect of this disclosure. The lateral sectional view is obtained based on a section starting from the axis BB and continuing in the direction of the depicted corresponding arrow.

Figure 22A:
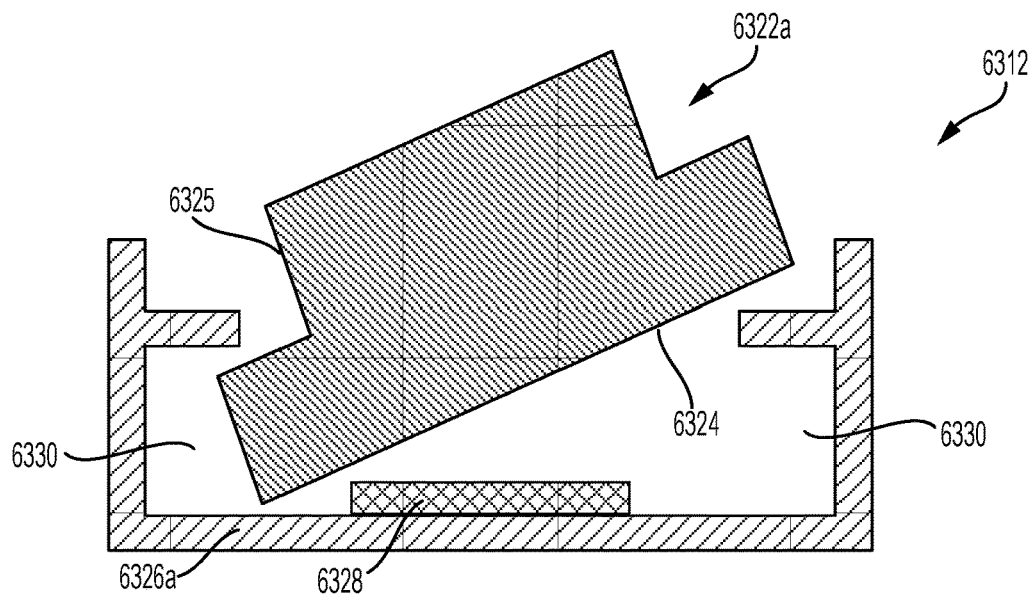
FIGS. 22A-22C illustrate an assembly process of an electrode of the ultrasonic surgical instrument shown in FIG. 18, into the recessed receiving portion, according to one aspect of this disclosure.
Figure 22B:
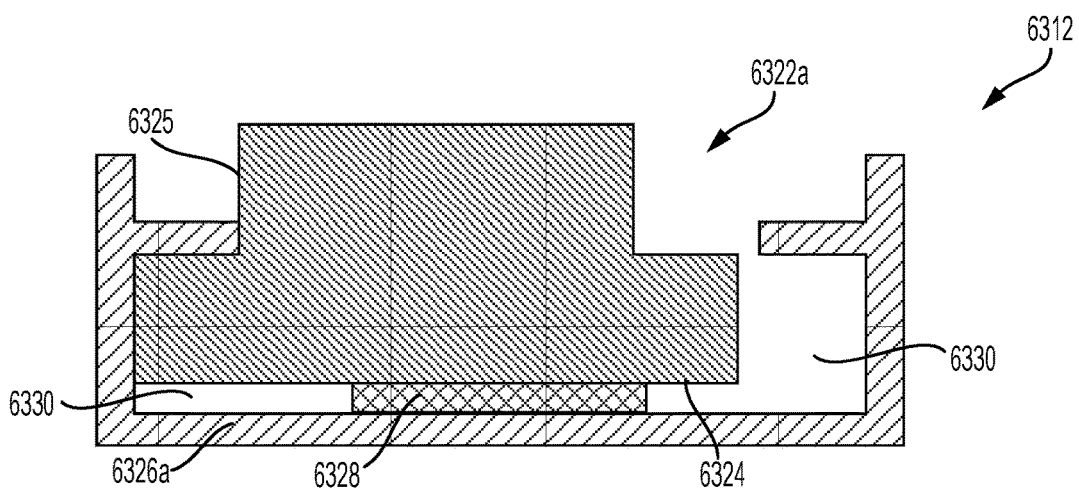
Figure 22C:
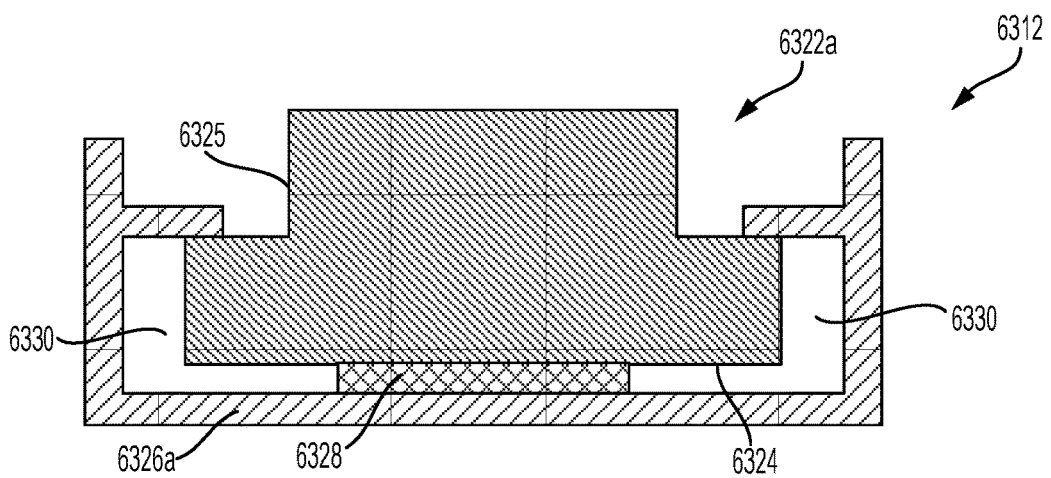

FIGS. 22A-22C illustrate an assembly process of the electrode 6322a into the recessed receiving portion 6326a, according to one aspect of this disclosure. FIG. 22A shows a side view of the electrode 6322a positioned at an angle such that one end of the base portion 6324 is located within the receiving area 6330 and the other end of the base portion 6324 is located outside of the receiving area 6330. As shown in FIG. 22A, the other end and the protruding portion 6325 both protrude away from the recessed receiving portion 6326a. Additionally, the electrode 6322a is not in contact with the molded interconnect pad 6328. FIG. 22B shows the one end of the base portion 6324 positioned into the receiving area 6330 such that the one end engages a first side wall and an arm 6332 (proximal to the first wall) of the recessed receiving portion 6326a in a slight interference fit. As can be seen in FIG. 22B, the electrode 6322a transitions from the initial angled position to a substantially flat or level position and moves in a direction towards the first side wall. The other end of the base portion 6324 is positioned away from a second side wall and another arm 6332 (proximal to the second side wall). The protruding portion 6325 remains protruding away from the recessed receiving portion 6326a. In one aspect, the arms 6332 extend from opposing side walls of the recessed receiving portion 6326a. FIG. 22C shows the electrode 6322a in a final position for compressing the piezoelectric element 6316a based on moving in an opposing direction towards the second side wall. In the final position, portions of the top sides of both ends of the base portion 6324 engage respective arms 6332. The remaining portions of the top sides of both ends of the base portion 6324 are uncontacted. Moreover, neither end of the base portion 6324 is in contact with either of the first or second side wall. The protruding portion 6325 remains protruding away from the recessed receiving portion 6326a. As shown in the aspects of FIGS. 22B-22C, the molded interconnect pad 6328 is electrically coupled to the electrode 6322a.

FIGS. 23A-23B illustrate an assembly process of the transducer assembly 6312 with electrodes 6322a, 6322b assembled from an initial uncompressed state to a final compressed state, relative to the piezoelectric elements 6316a, 6316b, according to one aspect of this disclosure. As shown in FIG. 23A, in one aspect, the transducer assembly 6312 includes two electrodes 6322a, 6322b configured to compress the piezoelectric elements 6316a, 6316b, respectively. Each of the two electrodes 6322a, 6322b is inserted in the receiving areas 6330 of the recessed receiving portions 6326a, 6326b, as described in connection with FIGS.

22A-22C. The two recessed receiving portions 6326a, 6326b in the initial uncompressed state as shown in FIG. 23A may be combined to form a unitary assembled component in the final compressed state. Specifically, the side walls of the recessed receiving portion 6326a are pressed against or combined with the side walls of the recessed receiving portion 6326b. The recessed receiving portion 6326a is transitioned in a direction towards the piezoelectric element 6316a and the recessed receiving portion 6326b is transitioned in a direction towards the piezoelectric element 6316b. FIG. 23B shows the transducer assembly 6312 with the unitary assembled component.

As can be seen in FIG. 23B, the first side walls of the two recessed receiving portions 6326a, 6326b combine to form one connected side wall of the unitary assembled component. Similarly, the second side walls of the two recessed receiving portions 6326a, 6326b combine to form another connected side wall of the unitary assembled component. In the final compressed state depicted in FIG. 23B, a top surface of each protruding portion 6325 of the electrodes 6322a, 6322b compresses against a corresponding surface of the piezoelectric elements 6316a, 6316b, respectively. Advantages of the compressed electrode configuration of the transducer assembly 6312 may include reduced assembly time, steps, and costs. Additionally, the configuration may result in an improved electrical connection between the piezoelectric elements 6316a, 6316b and waveguide 6320.

Figure 24:
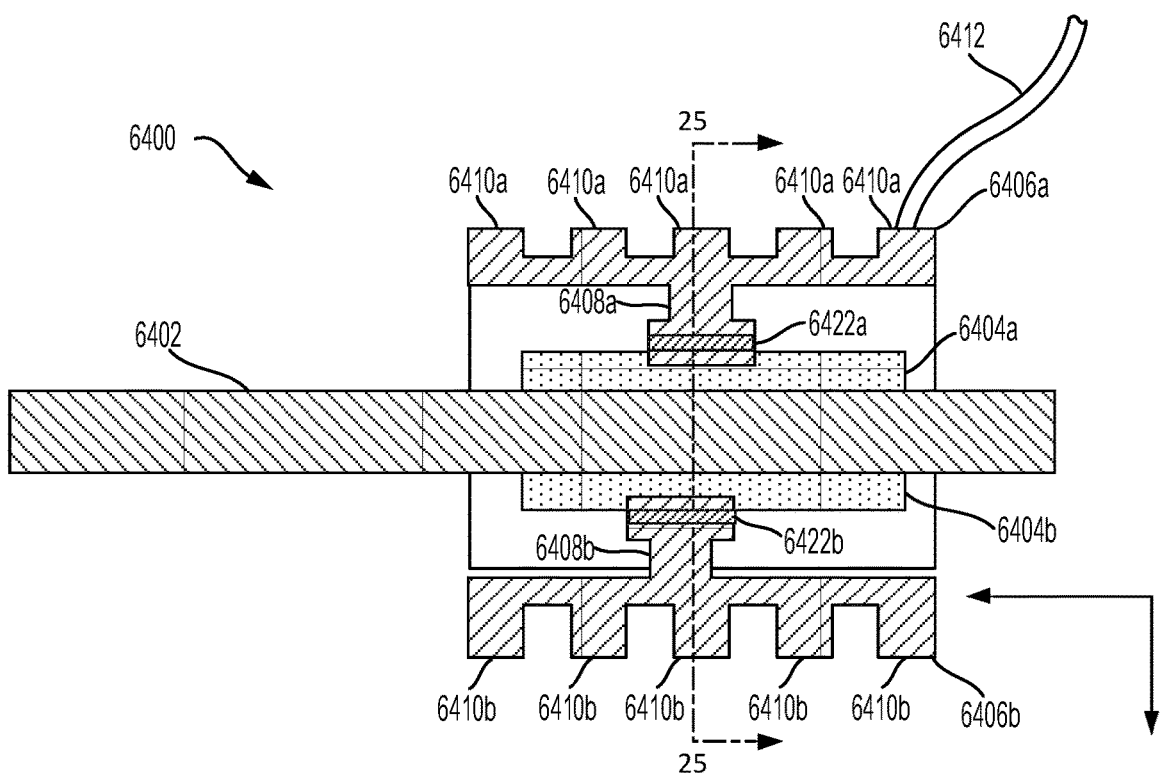
FIG. 24 shows aspects of an ultrasonic surgical instrument, which is configured to operate in a D31 mode of operation, according to one aspect of this disclosure.

FIG. 24 shows aspects of an ultrasonic surgical instrument 6400, which is configured to operate in a D31 mode of operation, according to one aspect of this disclosure. The ultrasonic surgical instrument 6400 may be the same as or substantially similar to the ultrasonic surgical instrument 6300. As seen in the side sectional view of FIG. 24, the ultrasonic surgical instrument 6400 includes a waveguide 6402, piezoelectric elements 6404a, 6404b, heat sink 6406a, 6406b, and an electrical connector such as a wire 6412. In one aspect, the heat sink 6406a, 6406b comprises a metal housing with two heat sink component halves. The upper heat sink half 6406a may be positioned on a top surface of the waveguide 6402 while the lower heat sink half 6406b may be positioned on a bottom surface of the waveguide 6402. The metal housing can be made of a suitable metal, such as aluminum or steel. Each of the heat sink halves 6406a, 6406b comprises a rib 6408a, 6408b, and a plurality of fins 6410a, 6410b. Suitable bonding material, such as conductive foam or grease 6422a, 6422b, may be used to thermally and electrically couple each of the ribs 6408a, 6408b to the piezoelectric elements 6404a, 6404b, respectively. Additionally, the conductive foam or grease 6422a, 6422b are adhesives to securely adhere the ribs 6408a, 6408b to the piezoelectric elements 6404a, 6404b. In another aspect, thermal energy or heat generated during operation of the piezoelectric elements 6404a, 6404b may be dissipated through the plurality of fins 6410a, 6410b. In particular, the heat sink 6406a, 6406b functions based on conducting heat generated from either of the piezoelectric elements 6404a through the corresponding rib 6408a, 6408b and away from the ultrasonic surgical instrument 6400 via one or more of the corresponding fins 6410a, 6410b. Each of the plurality of fins 6410a, 6410b may be spaced at a predetermined interval apart. Specifically, there may be a recessed space between adjacent fins 6410a, 6410b, except for the fins 6410a, 6410b located at an end of the heat sink halves 6406a, 6406b.

Figure 25:
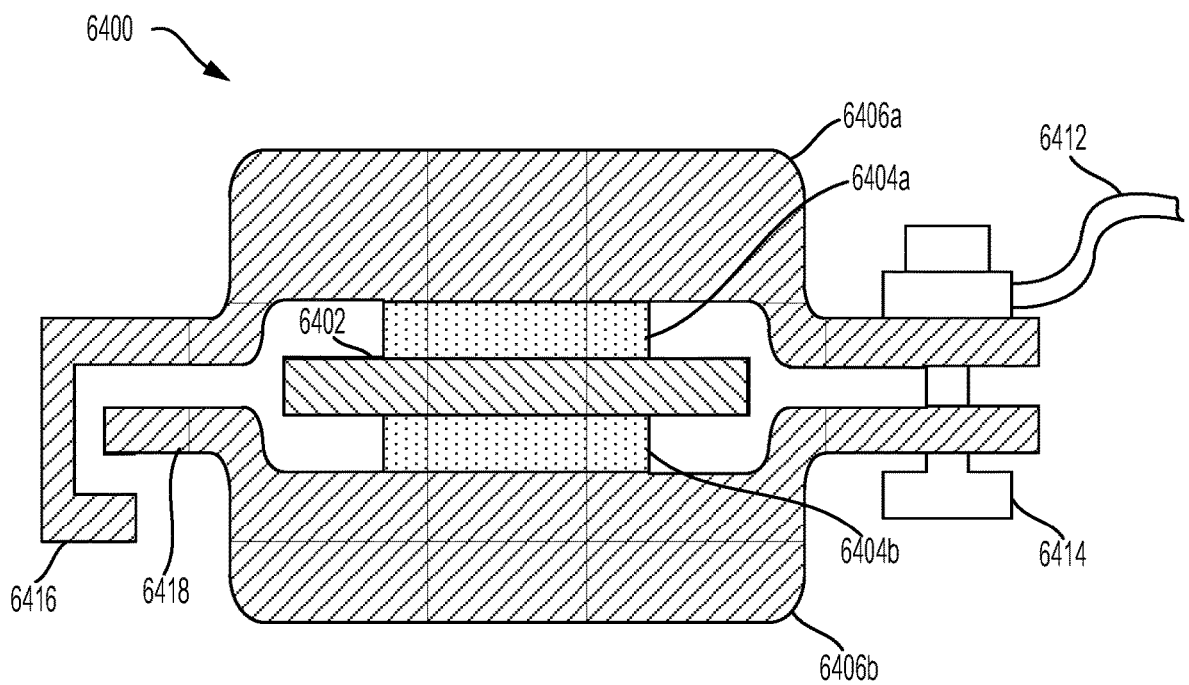
FIG. 25 is a sectional view of the ultrasonic surgical instrument shown in FIG. 24 taken along section line 25-25 as shown in FIG. 24, according to one aspect of this disclosure.

In yet another aspect, as shown in FIG. 24, the wire 6412 is positioned or wedged between the heat sink halves 6406a, 6406b and is configured to be electrically connected to an ultrasonic signal generator. FIG. 25 is a sectional view of the ultrasonic surgical instrument 6400 taken along section line 25-25 as shown in FIG. 24, according to one aspect of this disclosure. As shown in FIG. 25, in one aspect, the upper heat sink half 6406a comprises a receiving portion 6416 at a proximal end. The lower heat sink half 6406b comprises an inserting portion 6418 at a proximal end. The inserting portion 6418 is configured to engage or be inserted into the receiving portion 6416 in an interference fit for coupling the lower and upper heat sink halves 6406a, 6406b to each other. In another aspect, a fastener device 6414, such as a locking screw or pop rivet, for example, is used to secure the two heat sink halves 6406a, 6406b together such that the halves 6406a, 6406b form the unitary metal housing of the heat sink 6406a, 6406b.

Figure 26:
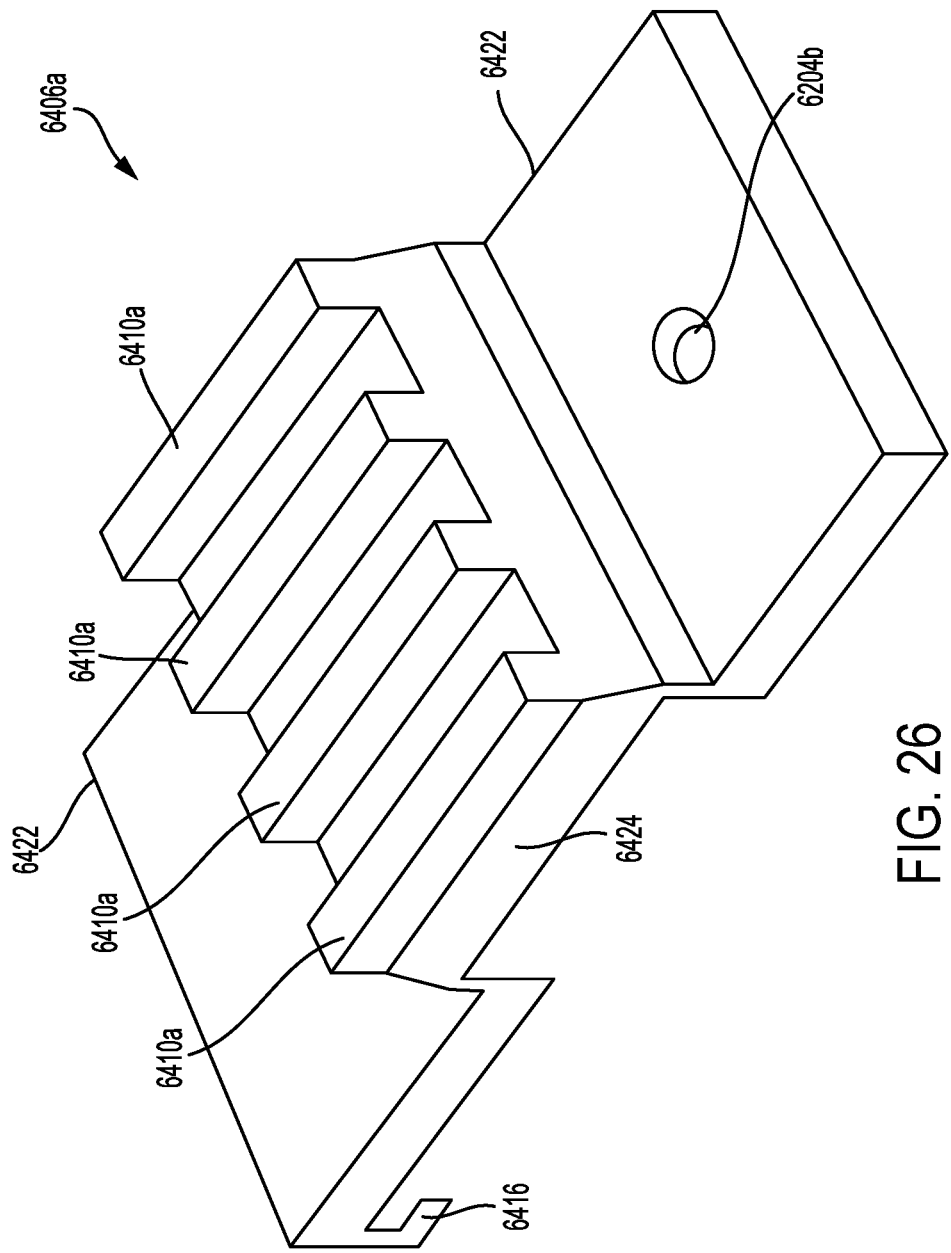
FIG. 26 is a perspective view of an upper heat sink half of the ultrasonic surgical instrument shown in FIG. 24, according to one aspect of this disclosure.

FIG. 26 is a perspective view of the upper heat sink half 6406a, according to one aspect of this disclosure. In one aspect, as shown in FIG. 26, the receiving portion 6416 extends in a direction towards the waveguide 6402 such that the receiving portion 6416 defines a space for the inserting portion 6418. As can be seen in FIG. 26, the upper heat sink half 6406a comprises a base portion 6422, which is interrupted by a protruding portion 6424 extending away (i.e., upwards) from the piezoelectric element 6404a. The protruding portion 6424 comprises the plurality of fins 6410a, which may be mounted to or extend from the top surface of the protruding portion 6424. As described above, the plurality of fins 6410a may be spaced at a predetermined interval apart. As shown in FIG. 26, the base portion 6422 and the protruding portion 6424 form an interconnected component of the upper heat sink half 6406a via an interconnecting portion. The rib 6408a (not shown in FIG. 26) can be coupled to the bottom surface of the protruding portion and connected to the piezoelectric element 6404a through the conductive foam or grease 6422a, as described above. In another aspect, the lower heat sink half 6406b may be similar to upper heat sink half 6406a except that the base portion of the lower heat sink half 6406b can be interrupted by a protruding portion extending away (i.e., downwards) from the piezoelectric element 6404b. The protruding portion may comprise the plurality of fins 6410b.

Figure 27:
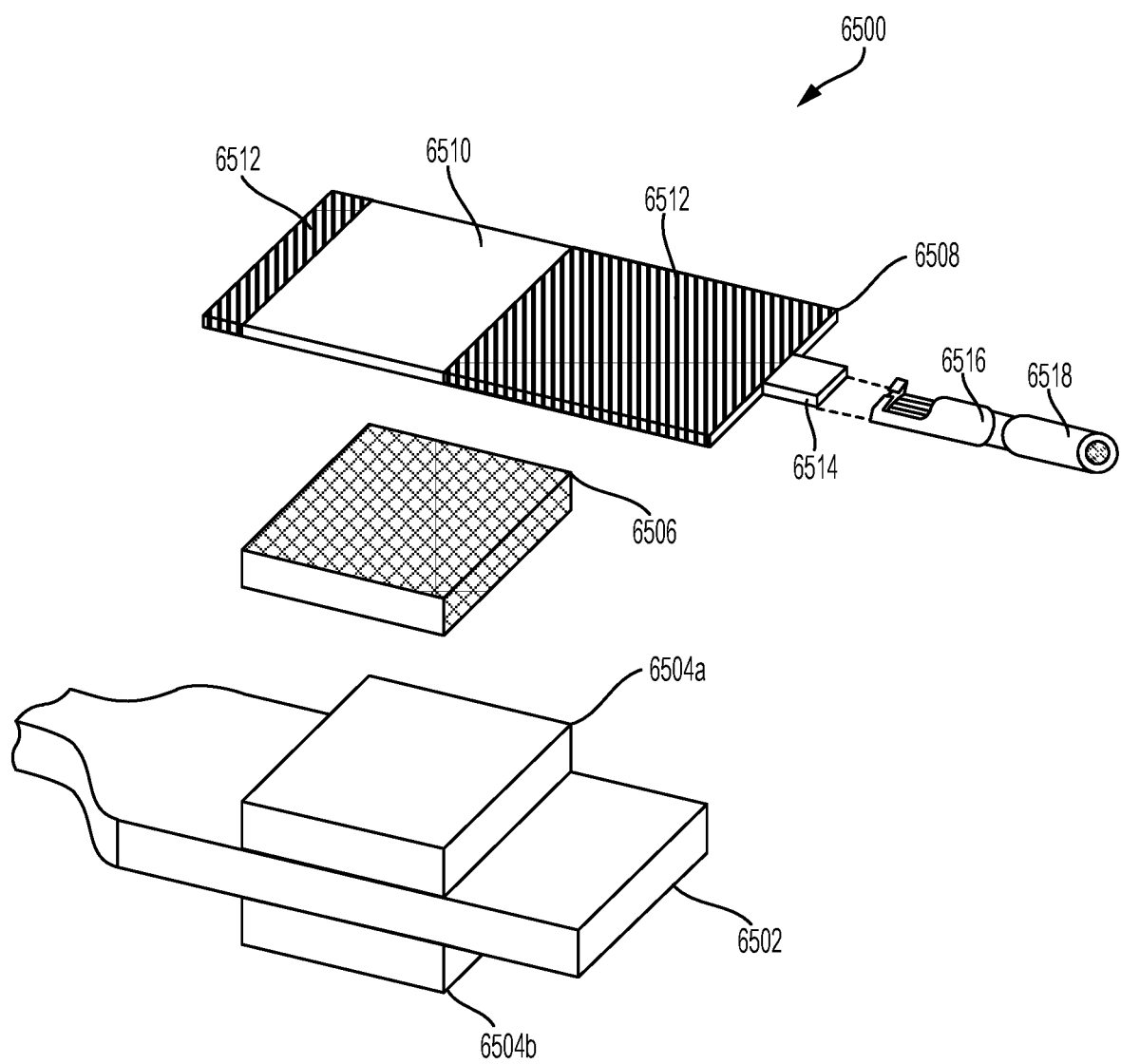
FIG. 27 is a perspective view of an ultrasonic surgical instrument, which is configured to operate in a D31 mode of operation, according to one aspect of this disclosure.

FIG. 27 is a perspective view of an ultrasonic surgical instrument 6500, which is configured to operate in a D31 mode of operation, according to one aspect of this disclosure. The ultrasonic surgical instrument 6500 comprises a waveguide 6502, piezoelectric elements 6504a, 6504b, a conductive bridge 6506, a heat sink 6508, a crimp connector 6516, and a wire 6518. The piezoelectric elements 6504a, 6504b are positioned on opposite surfaces of the waveguide 6502. In one aspect, the conductive bridge 6506 is both thermally and electrically conductive. The conductive bridge 6506 can be a thermal foam gasket (TFG), which is constructed from a graphite sheet over a foam core. For example, the graphite sheet could be formed from suitable graphite material such as eGRAF® SPREADERSHIELD™ or eGRAF® HITHERM™ flexible graphite thermal interface materials (TIMs), both available from GrafTech International Holdings Inc. of Brooklyn Heights, Ohio. The graphite sheet may be wrapped or positioned over a plurality of the surfaces of the foam core. The SPREADERSHIELD™ flexible graphite has an in-plane thermal conductivity range of, for example, 300 to 1500 watts per meter Kelvin (W/mK). In contrast, aluminum has a thermal conductivity range of about 200 to 250 W/mK. The foam core can be formed from suitable thermoplastic elastomers (TPEs), such as thermoplastic polyurethanes or thermally conductive silicone gap fillers available from Stockwell Elastomerics, Inc. of Philadelphia, Pa. The foam core may also be made of nickel & copper (Ni/Cu) metallized urethane conductive foam. Similarly, the top and bottom surfaces of the conductive foam can be made of Ni/Cu knit polyester mesh.

In other aspects, the conductive bridge 6506 could be a foil over foam gasket such as the SOFT-SHIELD 4000 Series electromagnetic interference (EMI) gasket (comprising a PORON1 Urethane Foam core) available from Parker Hannifin Corporation of Cleveland, Ohio, or a suitable metallized fabric over foam gasket available from Laird Technologies of Warren, Ohio. In another aspect, the conductive bridge 6506 is configured be electrically coupled to a metal electrode shim 6508, such as to electrically bridge or conduct signals (e.g generated by an ultrasonic signal generator) passing from the shim 6508 through the bridge 6506 to the piezoelectric element 6504*a*. The shim 6508 is configured to compress the piezoelectric element 6504*a* against the waveguide 6502. As shown in FIG. 27, the shim 6508 comprises two coated, electrically non-conductive portions 6512 that are interrupted by a conductive portion 6510. The conductive portion 6510 of the shim 6508 is configured to be positioned over the conductive bridge 6506 such that the bottom surface of the conductive portion 6510 is in electrical and thermal contact with the top surface of the conductive bridge 6506. Moreover, the bottom surface of the conductive bridge 6506 can be positioned over piezoelectric element 6504*a*. Thus, piezoelectric element 6504*a*, conductive bridge 6506 and shim 6508 are all thermally and electrically coupled to each other.

Accordingly, the shim 6508 operates as a heat sink and a compressive electrode for the ultrasonic surgical instrument 6500. In particular, thermal energy or heat generated during operation of the piezoelectric element 6504*a* may be conducted through the conductive bridge 6506 to be absorbed and dissipated by the shim 6508 heat sink. Additionally, electrical energy may be conducted from a generator through the conductive portion 6510 of the shim 6508 and the conductive bridge 6506 to the piezoelectric element 6504*a*. In one aspect, the safe operating temperature of the piezoelectric elements 6504*a*, 6504*b* is below 150 degrees Celsius (i.e., temperature to ensure against damage to the piezoelectric elements 6504*a*, 6504*b*). A flange or attachment component 6514 may be configured to be received within a receiving portion of the crimp connector 6516. The crimp connector 6516 can be electrically coupled to the wire 6518, which can be connected to the generator. In various aspects, a second conductive bridge 6506 and shim 6508 may be located below the bottom surface of the piezoelectric element 6504*b* in a similar but symmetrical configuration to the configuration described above (i.e., the conductive bridge 6506 and shim 6508 located above the piezoelectric element 6504*a*). Specifically, the top surface of the second conductive bridge 6506 may be positioned below the bottom surface of the piezoelectric element 6504*b* and the top surface of the second conductive portion 6510 of the second shim 6508 may be positioned below the bottom surface of the second conductive bridge 6506. Advantages of the bridge and shim configuration of the ultrasonic surgical instrument 6500 may include reduced costs, easier manufacture and assembly, and efficiency based on using the shim 6508 heat sink as an electrical connection.

Figure 28:
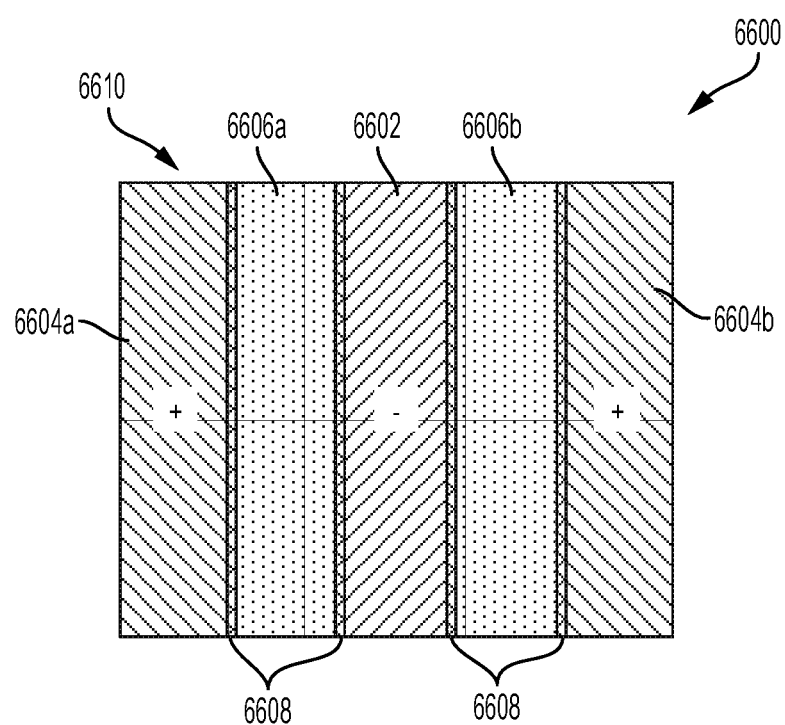
FIG. 28 illustrates a D31 ultrasonic surgical instrument that includes piezoelectric elements attached on one side to an ultrasonic waveguide by a conductive adhesive and attached on another side to electrically conductive plates by a conductive adhesive, according to one aspect of this disclosure.

FIG. 28 illustrates an ultrasonic surgical instrument 6600 including an ultrasonic transducer 6610 attached to an ultrasonic waveguide 6602, by a bonding material, where the ultrasonic surgical instrument 6600 is configured to operate in a D31 mode, according to one aspect of this disclosure. The ultrasonic transducer 6610 includes piezoelectric elements 6606*a*, 6606*b* attached on opposite sides of the ultrasonic waveguide 6602 by a bonding material. In one aspect, the bonding material is a conductive adhesive 6608. Conductive plates 6604*a*, 6604*b* are attached to the piezoelectric elements 6606*a*, 6606*b*, respectively, by a bonding material such as a conductive adhesive 6608, according to one aspect of this disclosure. An electrical connection method includes soldering the piezoelectric elements 6606*a*, 6606*b* on one side directly to the inside surfaces of the electrically conductive plates 6604*a*, 6604*b* (e.g., copper plates or sheets) and on the other side to the ultrasonic waveguide 6602. A conductive epoxy 6608 is applied between the electrically conductive plates 6604*a*, 6604*b* and the free ends of the piezoelectric elements 6606*a*, 6606*b*. A conductive epoxy 6608 also is applied between the fixed ends of the piezoelectric elements 6606*a*, 6606*b* and the ultrasonic waveguide 6602. Electrically conductive elements such as wires may be connected to the electrically conductive plates 6606*a*, 6606*b* and to the ultrasonic waveguide 6602. In one aspect, the ultrasonic waveguide 6602 may be formed by stamping and electrical connection features may be added to the ultrasonic waveguide 6602. The electrically conductive plates 6606*a*, 6606*b* may be formed of copper sheets and assembled to female electrical connectors on a cable. Crimp connections may be stamped or formed on the ultrasonic waveguide 6602 and the electrically conductive plates 6606*a*, 6606*b* (e.g., copper sheets). The connections to wires may be crimped during assembly. In various aspects, the electrical connection process may include any combination of the above.

Figure 29:
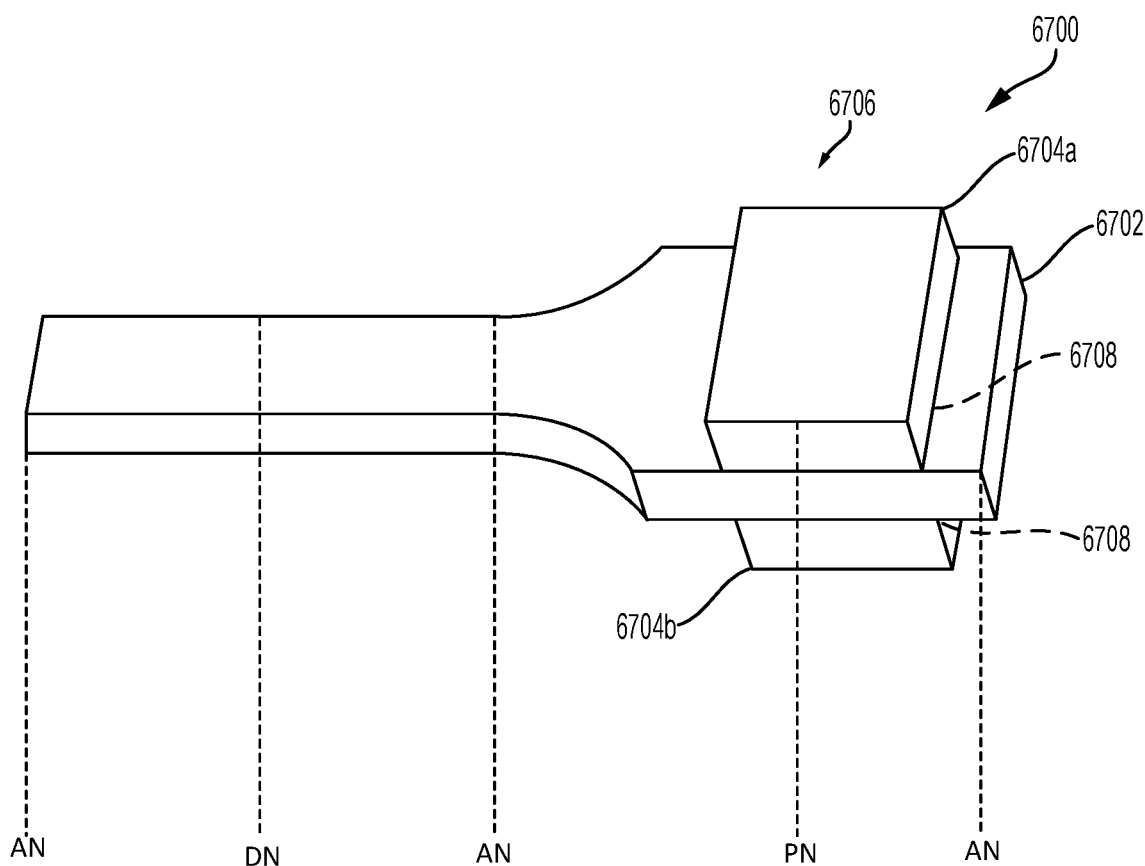
FIG. 29 is a perspective view of an ultrasonic surgical instrument, which is configured to operate in a D31 mode of operation, according to one aspect of this disclosure.

FIG. 29 is a perspective view of an ultrasonic surgical instrument 6700, which is configured to operate in a D31 mode of operation, according to one aspect of this disclosure. The ultrasonic surgical instrument 6700 comprises an ultrasonic waveguide 6702, and piezoelectric elements 6704*a*, 6704*b*. The ultrasonic surgical instrument 6700 includes an ultrasonic transducer 6706 that includes the piezoelectric elements 6704*a*, 6704*b*. As shown in FIG. 14, the piezoelectric elements 6704*a*, 6704*b* are attached to the ultrasonic waveguide 6702 using a bonding material such as a conductive epoxy adhesive 6708 to bond the piezoelectric elements 6704*a*, 6704*b* to the ultrasonic waveguide 6702. Specifically, epoxy adhesive 6708 is applied to the area between the bottom surface of the first piezoelectric element 6704*a* and the top surface of the ultrasonic waveguide 6702. Similarly, epoxy adhesive 6708 is applied to the area between the bottom surface of the ultrasonic waveguide 6702 and the top surface of the second piezoelectric element 6704*b*. In one aspect, the use of the epoxy adhesive 6708 creates a secure electrical connection between the piezoelectric elements 6704*a*, 6704*b* and the ultrasonic waveguide 6702. As described above, the electrical ground connection can be made to the ultrasonic waveguide 6702, which is electrically conductive.

As shown in FIG. 29, the locations of a plurality of nodes and antinodes are depicted. Dashed lines "PN" and "DN" indicate a proximal and a distal node, respectively. Each of the dashed lines "AN" indicates an anti-node. As described above, a minimum or zero crossing in the vibratory motion standing wave is generally referred to as a node and an absolute value maximum or peak in the standing wave is generally referred to as an anti-node. Conventionally, the electrical ground connection is made at a proximal node, which is denoted by the dashed lines "PN" in FIG. 29. The location of the proximal node may be represented by a longitudinal line extending through a center portion of the piezoelectric elements 6704a, 6704b and ultrasonic waveguide 6702. Furthermore, the proximal node represents a location of high voltage potential, which enables an electrical ground connection to be made to the ultrasonic waveguide 6702 based on the electrical contact between the piezoelectric elements 6704a, 6704b and the ultrasonic waveguide 6702. In another aspect, the use of the epoxy adhesive 6708 may enable the ultrasonic waveguide 6702 electrical ground connection to be made at an alternate node, such as the distal node, instead of the proximal node. An alternate node may be used because the use of the epoxy adhesive 6708 creates a secure electrical contact between the piezoelectric elements 6704a, 6704b and the ultrasonic waveguide 6702.

Figure 30:
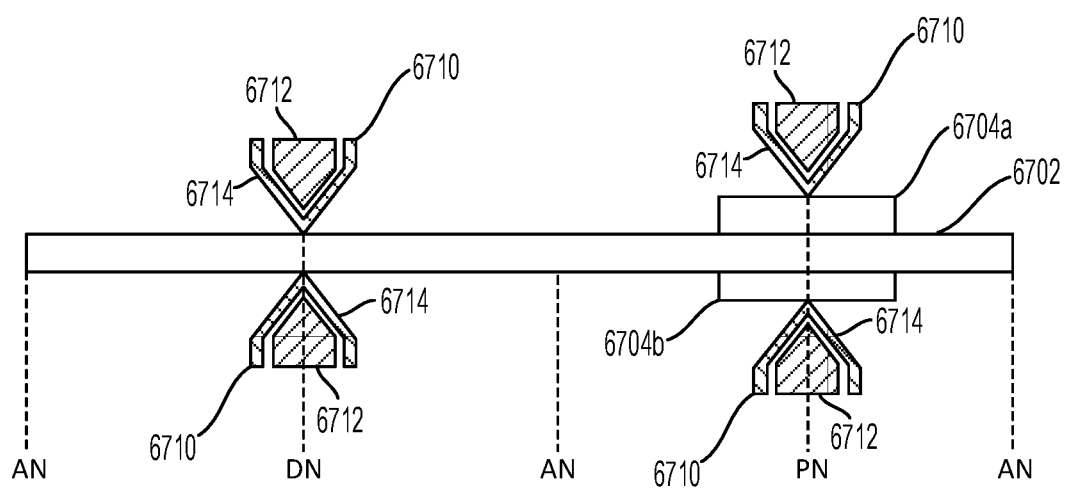
FIG. 30 is a sectional view of the ultrasonic surgical instrument shown in FIG. 29 with electrically conductive electrodes configured to compress the piezoelectric elements and the ultrasonic waveguide, according to one aspect of this disclosure.

FIG. 30 is a sectional view of the ultrasonic surgical instrument 6700 with electrically conductive electrodes 6710 configured to compress the piezoelectric elements 6704a, 6704b and the ultrasonic waveguide 6702, respectively. The electrically conductive electrodes 6710 each comprise a compliant member portion 6712 and a thin metal portion 6714. In one aspect, two conductive electrodes 6710 are positioned on each side of the ultrasonic waveguide 6702. At the proximal node, the thin metal portion 6714 of a first upper conductive electrode 6710 comprises a narrow tip to compress the piezoelectric element 6704a. Similarly, at the proximal node, the thin metal portion 6714 of a first lower conductive electrode 6710 comprises a narrow tip to compress the piezoelectric element 6704a. At the distal node, the thin metal portion 6714 of a second upper conductive electrode 6710 comprises a narrow tip to compress the ultrasonic waveguide 6702. Similarly, at the distal node, the thin metal portion 6714 of a second lower conductive electrode 6710 comprises a narrow tip to compress the ultrasonic waveguide 6702. In another aspect, based on the second upper conductive electrode 6710 and the second lower conductive electrode 6710, an electrical ground connection may be applied to the ultrasonic waveguide at the distal node. Advantages of this configuration may include reduced manufacturing complexity of the ultrasonic surgical instrument 6700.

Figure 31A:
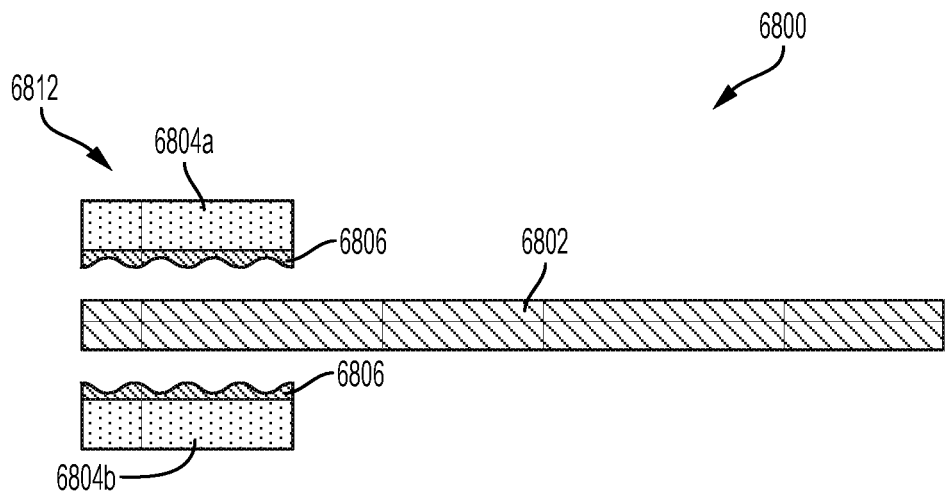
FIG. 31A illustrates an ultrasonic surgical instrument prior to assembly and poling, according to one aspect of this disclosure.
Figure 31B:
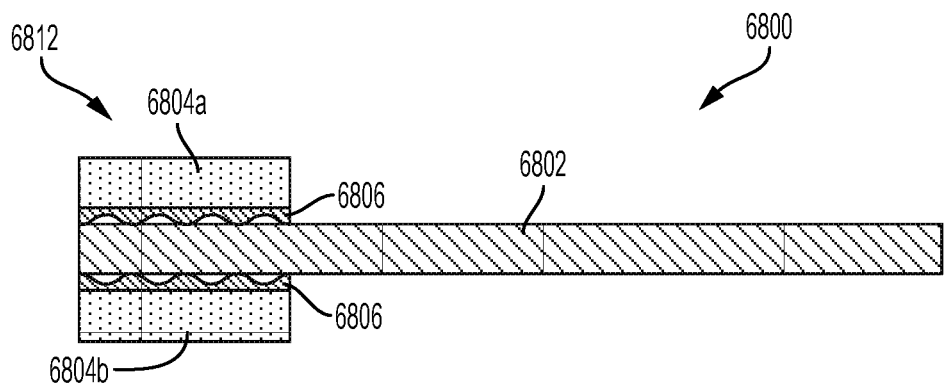
FIG. 31B illustrates the ultrasonic surgical instrument of FIG. 31A prior to poling and the first and second unpoled piezoelectric elements secured to the ultrasonic waveguide in a D31 configuration, according to one aspect of this disclosure.
Figure 31C:
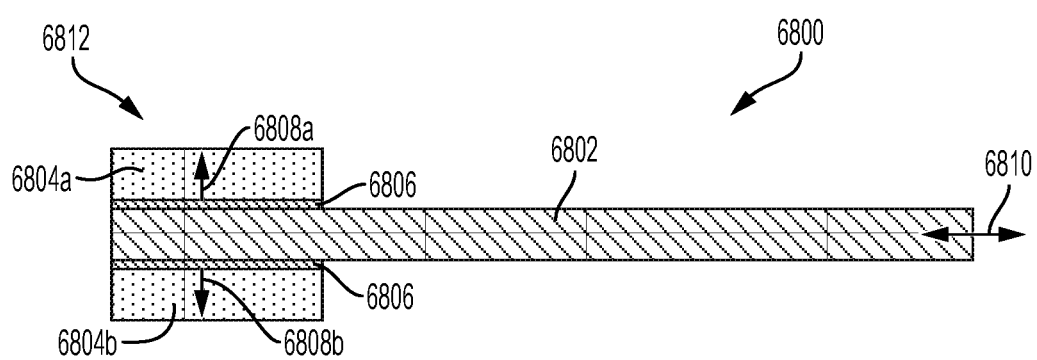
FIG. 31C illustrates the ultrasonic instrument of FIG. 31B prior to poling and the first and second unpoled piezoelectric elements secured to the ultrasonic waveguide in a D31 configuration, according to one aspect of this disclosure.

FIGS. 31A-31C illustrate an ultrasonic surgical instrument 6800 that includes an ultrasonic waveguide 6802 attached to an ultrasonic transducer 6812 by a bonding material, where the ultrasonic surgical instrument 6800 is configured to operate in a D31 mode. The ultrasonic transducer 6812 includes first and second unpoled piezoelectric elements 6804a, 6804b attached to opposite sides of the ultrasonic waveguide 6802 by a bonding material. FIG. 31A illustrates an ultrasonic surgical instrument 6800 prior to assembly and poling, according to one aspect of this disclosure. The ultrasonic surgical instrument 6800 includes a metal ultrasonic waveguide 6802 (e.g., titanium/titanium alloy). A bonding material such as solder paste 6806 is applied to one surface of a first unpoled piezoelectric element 6804a and a second unpoled piezoelectric element 6804b. The solder paste 6806 is a sticky mixture of flux and tiny solder particles, and may be applied to piezoelectric elements 6804a, 6804b with a stainless steel or nickel stencil using a screen printing process. The solder paste 6806 also can be applied to the piezoelectric elements 6804a, 6804b by a jet-printing mechanism, similar to an inkjet printer. After pasting, the piezoelectric elements 6804a, 6804b proceed to a pick-and-place machine or a manual placing process for securing the piezoelectric elements 6804a, 6804b to the ultrasonic waveguide 6802.

FIG. 31B illustrates the ultrasonic surgical instrument 6800 of FIG. 31A prior to poling with the first and second unpoled piezoelectric elements 6804a, 6804b secured to the ultrasonic waveguide 6802 in a D31 configuration, according to one aspect of this disclosure. After pasting, the piezoelectric elements 6804a, 6804b are secured to the ultrasonic waveguide 6802 using an automated or manual process. An insulating clamp may be employed to secure the first and second unpoled piezoelectric elements 6804a, 6804b prior to conveying the secured piezoelectric elements 6804a, 6804b and ultrasonic waveguide 6802 assembly to a reflow soldering oven. Once in the oven, the solder paste 6806 is reflowed to bond the first and second unpoled piezoelectric elements 6804a, 6804b to the ultrasonic waveguide 6802.

FIG. 31C illustrates the ultrasonic instrument 6800 of FIG. 31B after reflow soldering and prior to poling the first and second unpoled piezoelectric elements 6804a, 6804b attached to the ultrasonic waveguide 6802 in a D31 configuration, according to one aspect of this disclosure. Once the secured piezoelectric elements 6804a, 6804b and ultrasonic waveguide 6802 assembly is conveyed to a reflow soldering oven, the solder paste 6806 is reflowed to establish a bond between the first and second unpoled piezoelectric elements 6804a, 6804b and the ultrasonic waveguide 6802. The solder paste 6806 may be reflowed using standard surface mount technology. There are a number of techniques for reflowing the solder 6806. One technique employs infrared lamps and is called infrared reflow. Another technique employs hot gas convection using either standard air or nitrogen gas. Another surface mount technology employs special fluorocarbon liquids with high boiling points which use a method called vapor phase reflow. Each method has its advantages and disadvantages.

After the first and second unpoled piezoelectric elements 6804a, 6804b are attached to the ultrasonic waveguide 6802 using a reflow solder technique, the entire ultrasonic instrument 6800 assembly is poled. A poling process may be carried out in an oil bath with special fixturing. The nature of the piezoelectric effect is closely related to the occurrence of electric dipole moments in solids. The latter may be induced for ions on crystal lattice sites with asymmetric charge surroundings as in piezoelectric elements. The dipole density or polarization (dimensionality ($C \cdot m/m^3$)) may be calculated for crystals by summing up the dipole moments per volume of the crystallographic unit cell. As every dipole is a vector, the dipole density P is a vector field. Dipoles near each other tend to be aligned in regions called Weiss domains. The domains are usually randomly oriented, but can be aligned using the process of poling (not the same as magnetic poling), a process by which a strong electric field is applied across the material, usually at elevated temperatures. Not all piezoelectric materials can be poled. The poling axis (P) of the piezoelectric elements 6804a, 6804b is indicated by the direction arrows 6808a, 6808b, respectively. The motion axis of the ultrasonic waveguide 6802 in response to excitation of the piezoelectric elements 6804a, 6804b is shown by the motion arrow 6810 at the distal end of the ultrasonic waveguide 6802 generally referred to as the ultrasonic blade portion of the ultrasonic waveguide 6802. The motion axis 6810 is orthogonal to the poling axis (P) 6808a, 6808b.

The piezoelectric effect is the change of polarization P under the application of a mechanical stress. This might either be caused by a reconfiguration of the dipole-inducing surrounding or by re-orientation of molecular dipole moments under the influence of the external mechanical stress. Piezoelectricity may manifest in a variety of ways, including the variation of the polarization strength, its direction or both, with the details depending on: the orientation of P within the crystal; crystal symmetry; and the applied mechanical stress. The change in P appears as a variation of surface charge density upon the crystal faces, i.e., as a variation of the electric field extending between the faces caused by a change in dipole density in the bulk. For example, a 1 cm$^3$ cube of quartz with 2 kN (500 lbf) of correctly applied force can produce a voltage of 12500 V.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An ultrasonic surgical instrument comprising: a transducer base plate comprising a first and second face; a first piezoelectric element positioned on the first face; a second piezoelectric element positioned on the second face, wherein the first and second piezoelectric element are each configured to operate in a D31 mode with respect to a longitudinal axis of a waveguide coupled to the transducer base plate, wherein the waveguide is electrically coupled to the first piezoelectric element and to the second piezoelectric element by a conductive adhesive; an electrode configured to electrically couple the first and second piezoelectric elements to an ultrasonic signal generator; and a thermal conductor configured to conduct thermal energy away from the first and second piezoelectric elements.

Example 2

The ultrasonic surgical instrument of Example 1, wherein the first piezoelectric element has a poling axis in a direction from a first side to a second side of the first piezoelectric element and the second piezoelectric element has a poling axis in a direction from a first side to a second side of the second piezoelectric element to operate in the D31 mode.

Example 3

The ultrasonic surgical instrument of Example 1 or Example 2, wherein a motion axis of the ultrasonic waveguide is orthogonal to the poling axes of the first and second piezoelectric elements.

Example 4

The ultrasonic surgical instrument of one or more of Example 1 through 3, wherein the conductive adhesive is a solder bonding material.

Example 5

The ultrasonic surgical instrument of one or more of Example 1 through Example 4, further comprising an electrical connector positioned at one of a plurality of nodes of the ultrasonic surgical instrument, wherein the waveguide is coupled to the electrical connector to provide an electrical ground.

Example 6

The ultrasonic surgical instrument of one or more of Example 1 through Example 5, further comprising: a first electrically conductive plate attached to a second face of the first piezoelectric element by a second bonding material; and a second electrically conductive plate attached to a second face of the second piezoelectric element by the second bonding material.

Example 7

The ultrasonic surgical instrument of one or more of Example 1 through Example 6, wherein: the thermal conductor is a heat sink that comprises a metal housing including at least one fin, the metal housing comprises two portions interconnected through the waveguide, and the at least one fin is configured to conduct thermal energy away from the first and second piezoelectric elements through a rib of the heat sink.

Example 8

The ultrasonic surgical instrument of Example 7, wherein an electrical connector connected to the ultrasonic signal generator is wedged between the two portions.

Example 9

A method of fabricating an ultrasonic surgical instrument comprising: machining a transducer base plate from a portion of a flat metal stock, wherein the transducer base plate comprises a first and second face; positioning a first piezoelectric element on the first face; positioning a second piezoelectric element on the second face, wherein the first and second piezoelectric element are each configured to operate in a D31 mode with respect to a longitudinal axis of a waveguide coupled to the transducer base plate; coupling, by a first electrically conductive adhesive, the waveguide to the first piezoelectric element and the second piezoelectric element; compressing, by an electrode, against the first and second piezoelectric elements to electrically couple the first and second piezoelectric elements to an ultrasonic signal generator; and conducting, by a thermal conductor, heat away from the first and second piezoelectric elements.

Example 10

The method of Example 9, further comprising: forming a plurality of fins and a rib of the thermal conductor, wherein the conducted heat is conducted through the rib.

Example 11

The method of Example 10, further comprising: forming an interconnection between a first portion of the thermal conductor, the waveguide, and a second portion of the thermal conductor.

Example 12

The method of Example 11, wherein a first fin of the plurality of fins is positioned on the first portion, and a second fin of the plurality of fins is positioned on the second portion.

Example 13

The method of one or more Example 9 through Example 12, further comprising: applying a second electrically conductive adhesive between the electrode and the first and second piezoelectric elements.

Example 14

A transducer base plate comprising: a first and second face, wherein a first piezoelectric element is positioned on the first face and a second piezoelectric element is positioned on the second face, and wherein the first and second piezoelectric element are each configured to operate in a D31 mode with respect to a longitudinal axis of a waveguide coupled to the transducer base plate; a conductive adhesive to electrically couple the first and second piezoelectric elements to the waveguide; an electrode configured to electrically couple the first and second piezoelectric elements to an ultrasonic signal generator; and a thermal conductor configured to conduct heat away from the first and second piezoelectric elements.

Example 15

The transducer base plate of Example 14, further comprising: a third piezoelectric element positioned in a recess of the waveguide; an insulator positioned on a first portion of the electrode, wherein a second portion of the electrode is configured to electrically couple the first, second, and third piezoelectric elements to the ultrasonic signal generator.

Example 16

The transducer base plate of Example 15, wherein the electrode comprises the first portion, the second portion, and a third portion.

Example 17

The transducer base plate of one or more of Example 14 through Example 16, wherein the conductive adhesive comprises a first portion positioned at a proximal end of the first and second piezoelectric elements and a second portion positioned at a distal end of the first and second piezoelectric elements.

Example 18

The transducer base plate of one or more Example 14 through Example 17, further comprising a first recess for receiving the first piezoelectric element and a second recess for receiving the second piezoelectric element, wherein a length of the first recess is greater than a length of the first piezoelectric element such that a gap of the first recess is provided and a length of the second recess is greater than a length of the second piezoelectric element such that a gap of the second recess is provided.

Example 19

An ultrasonic transducer assembly comprising: a stack of a plurality of piezoelectric elements, wherein the stack is configured to operate in a D33 mode with respect to a longitudinal axis of a waveguide coupled to the transducer base plate; a compression plate to compress the stack of the plurality of piezoelectric elements to couple the stack of piezoelectric elements to a waveguide; and a compressive element for applying a compressive force against the compression plate.

Example 20

The ultrasonic transducer assembly of Example 19, wherein the compressive element is a screw fastened to the compression plate.

Example 21

The ultrasonic transducer assembly of Example 19, wherein the compressive element is a wedge element.

The invention claimed is:
1. An ultrasonic surgical instrument comprising:
a transducer base plate comprising a first and second face;
a first piezoelectric element positioned on the first face;
a second piezoelectric element positioned on the second face, wherein the first and second piezoelectric element are each configured to operate in a D31 mode with respect to a longitudinal axis of a waveguide coupled to the transducer base plate, wherein the waveguide is electrically coupled to the first piezoelectric element and to the second piezoelectric element by a conductive adhesive;
an electrode configured to electrically couple the first and second piezoelectric elements to an ultrasonic signal generator; and
a thermal conductor configured to conduct thermal energy away from the first and second piezoelectric elements.

2. The ultrasonic surgical instrument of claim 1, wherein the first piezoelectric element has a poling axis in a direction from a first side to a second side of the first piezoelectric element and the second piezoelectric element has a poling axis in a direction from a first side to a second side of the second piezoelectric element to operate in the D31 mode.

3. The ultrasonic surgical instrument of claim 2, wherein a motion axis of the waveguide is orthogonal to the poling axes of the first and second piezoelectric elements.

4. The ultrasonic surgical instrument of claim 1, wherein the conductive adhesive is a solder bonding material.

5. The ultrasonic surgical instrument of claim 1, further comprising:
an electrical connector positioned at one of a plurality of nodes of the ultrasonic surgical instrument, wherein the waveguide is coupled to the electrical connector to provide an electrical ground.

6. The ultrasonic surgical instrument of claim 1, further comprising:
a first electrically conductive plate attached to a first face of the first piezoelectric element by a second bonding material; and
a second electrically conductive plate attached to a second face of the second piezoelectric element by the second bonding material.

7. The ultrasonic surgical instrument of claim 1, wherein:
the thermal conductor is a heat sink that comprises a metal housing including at least one fin,
the metal housing comprises two portions interconnected through the waveguide, and
the at least one fin is configured to conduct thermal energy away from the first and second piezoelectric elements through a rib of the heat sink.

8. The ultrasonic surgical instrument of claim 7, wherein an electrical connector connected to the ultrasonic signal generator is wedged between the two portions.

9. A transducer base plate comprising:
a first and second face, wherein a first piezoelectric element is positioned on the first face and a second piezoelectric element is positioned on the second face, and wherein the first and second piezoelectric element are each configured to operate in a D31 mode with respect to a longitudinal axis of a waveguide coupled to the transducer base plate;
a conductive adhesive to electrically couple the first and second piezoelectric elements to the waveguide;
an electrode configured to electrically couple the first and second piezoelectric elements to an ultrasonic signal generator; and
a thermal conductor configured to conduct heat away from the first and second piezoelectric elements.

10. The transducer base plate of claim 9, further comprising:
a third piezoelectric element positioned in a recess of the waveguide;
an insulator positioned on a first portion of the electrode, wherein a second portion of the electrode is configured to electrically couple the first, second, and third piezoelectric elements to the ultrasonic signal generator.

11. The transducer base plate of claim 10, wherein the electrode comprises the first portion, the second portion, and a third portion.

12. The transducer base plate of claim 9, wherein the conductive adhesive comprises a first portion positioned at a proximal end of the first and second piezoelectric elements and a second portion positioned at a distal end of the first and second piezoelectric elements.

13. The transducer base plate of claim 9, further comprising a first recess for receiving the first piezoelectric element and a second recess for receiving the second piezoelectric element, wherein a length of the first recess is greater than a length of the first piezoelectric element such that a gap of the first recess is provided and a length of the second recess is greater than a length of the second piezoelectric element such that a gap of the second recess is provided.

* * * * *